(12) United States Patent
Seibel et al.

(10) Patent No.: US 7,616,986 B2
(45) Date of Patent: Nov. 10, 2009

(54) OPTICAL FIBER SCANNER FOR PERFORMING MULTIMODAL OPTICAL IMAGING

(75) Inventors: Eric Seibel, Seattle, WA (US); Xingde Li, Seattle, WA (US); Xiumei Liu, Seattle, WA (US)

(73) Assignee: University of Washington, Seattle, WA (US)

( * ) Notice: Subject to any disclaimer, the term of this patent is extended or adjusted under 35 U.S.C. 154(b) by 249 days.

(21) Appl. No.: 10/880,008

(22) Filed: Jun. 28, 2004

(65) Prior Publication Data

US 2004/0254474 A1    Dec. 16, 2004

Related U.S. Application Data

(63) Continuation-in-part of application No. 09/850,594, filed on May 7, 2001, now Pat. No. 6,975,898.

(51) Int. Cl.
*A61B 6/00*    (2006.01)

(52) U.S. Cl. .................. 600/476; 600/129; 600/130; 250/227.26; 250/234

(58) Field of Classification Search ......... 600/476–478, 600/129, 130, 163, 173, 160; 356/479, 497, 356/477, 450; 250/234, 227.26
See application file for complete search history.

(56) References Cited

U.S. PATENT DOCUMENTS

| | | | |
|---|---|---|---|
| 4,410,235 A | 10/1983 | Klement et al. | 350/96.18 |
| 4,695,163 A | 9/1987 | Schachar | 356/369 |
| 4,768,513 A | 9/1988 | Suzuki | |
| 5,074,642 A | 12/1991 | Hicks | 385/116 |
| 5,172,685 A | 12/1992 | Nudelman | |
| 5,247,174 A | 9/1993 | Berman | 250/235 |
| 5,272,330 A | 12/1993 | Betzig et al. | 250/216 |
| 5,321,501 A * | 6/1994 | Swanson et al. | 356/479 |
| 5,394,500 A | 2/1995 | Marchman | 385/123 |
| 5,425,123 A | 6/1995 | Hicks | 385/117 |
| 5,480,046 A | 1/1996 | Filas et al. | 216/7 |

(Continued)

FOREIGN PATENT DOCUMENTS

EP    0 713 672    5/1996

(Continued)

OTHER PUBLICATIONS

Bing Qi et al. "Dynamic Focus Control in High-Speed Optical Coherence Tomography Based on a Microelectromechanical Mirror." Optics Communications 232 (2004) 123-128. <www.elsevier.com/locate/optcom>.

(Continued)

*Primary Examiner*—Long V Le
*Assistant Examiner*—Amanda L. Lauritzen
(74) *Attorney, Agent, or Firm*—Ronald M. Anderson

(57) ABSTRACT

An optical fiber scanner is used for multiphoton excitation imaging, optical coherence tomography, or for confocal imaging in which transverse scans are carried out at a plurality of successively different depths within tissue. The optical fiber scanner is implemented as a scanning endoscope using a cantilevered optical fiber that is driven into resonance or near resonance by an actuator. The actuator is energized with drive signals that cause the optical fiber to scan in a desired pattern at successively different depths as the depth of the focal point is changed. Various techniques can be employed for depth focus tracking at a rate that is much slower than the transverse scanning carried out by the vibrating optical fiber. The optical fiber scanner can be used for confocal imaging, multiphoton fluorescence imaging, nonlinear harmonic generation imaging, or in an OCT system that includes a phase or frequency modulator and delay line.

30 Claims, 8 Drawing Sheets

U.S. PATENT DOCUMENTS

| | | | |
|---|---|---|---|
| 5,570,441 A | 10/1996 | Filas et al. | 385/43 |
| 5,703,979 A | 12/1997 | Filas et al. | 385/43 |
| 5,715,337 A | 2/1998 | Spitzer et al. | 385/4 |
| 5,727,098 A | 3/1998 | Jacobson | 385/31 |
| 6,046,720 A | 4/2000 | Melville et al. | 345/108 |
| 6,069,698 A * | 5/2000 | Ozawa et al. | 356/511 |
| 6,091,067 A | 7/2000 | Drobot et al. | 250/234 |
| 6,134,003 A * | 10/2000 | Tearney et al. | 356/479 |
| 6,161,035 A | 12/2000 | Furusawa | 600/476 |
| 6,191,862 B1* | 2/2001 | Swanson et al. | 356/479 |
| 6,211,904 B1 | 4/2001 | Adair et al. | 458/76 |
| 6,294,775 B1 | 9/2001 | Seibel et al. | 250/208.1 |
| 6,327,493 B1 | 12/2001 | Ozawa et al. | 600/476 |
| 6,370,422 B1* | 4/2002 | Richards-Kortum et al. | 600/478 |
| 6,485,413 B1* | 11/2002 | Boppart et al. | 600/160 |
| 6,549,801 B1* | 4/2003 | Chen et al. | 600/425 |
| 6,687,010 B1* | 2/2004 | Horii et al. | 356/479 |
| 7,023,558 B2* | 4/2006 | Fee et al. | 356/479 |
| 7,072,046 B2* | 7/2006 | Xie et al. | 356/479 |
| 7,158,234 B2* | 1/2007 | Uchiyama et al. | 356/479 |
| 7,170,610 B2* | 1/2007 | Knuttel | 356/456 |
| 7,189,961 B2* | 3/2007 | Johnston et al. | 250/234 |
| 7,349,098 B2* | 3/2008 | Li | 356/479 |
| 2001/0055462 A1 | 12/2001 | Seibel | 385/147 |
| 2002/0064341 A1 | 5/2002 | Fauver et al. | 385/25 |
| 2003/0004412 A1* | 1/2003 | Izatt et al. | 600/425 |
| 2003/0142934 A1* | 7/2003 | Pan et al. | 385/116 |
| 2004/0015049 A1 | 1/2004 | Zarr | 600/101 |
| 2004/0181148 A1* | 9/2004 | Uchiyama et al. | 600/425 |
| 2005/0111009 A1 | 5/2005 | Keightley et al. | 356/602 |
| 2005/0168751 A1* | 8/2005 | Horii et al. | 356/479 |
| 2006/0126064 A1 | 6/2006 | Bambot et al. | 356/337 |
| 2006/0187462 A1* | 8/2006 | Srinivasan et al. | 356/479 |
| 2006/0202115 A1 | 9/2006 | Lizotte et al. | 250/234 |
| 2007/0038119 A1* | 2/2007 | Chen et al. | 600/476 |
| 2007/0088219 A1* | 4/2007 | Xie et al. | 600/473 |
| 2007/0129601 A1* | 6/2007 | Johnston et al. | 600/109 |
| 2007/0213618 A1* | 9/2007 | Li et al. | 600/476 |
| 2008/0004491 A1* | 1/2008 | Karasawa | 600/101 |

FOREIGN PATENT DOCUMENTS

| | | |
|---|---|---|
| EP | 0 520 388 | 9/1996 |
| EP | 1 142 529 A1 | 10/2001 |
| EP | 0 712 032 | 12/2001 |
| JP | 2001174744 A2 | 6/2001 |
| WO | WO 01/97902 | 12/2001 |

OTHER PUBLICATIONS

D. Huang, E.A. Swanson, C.P. Lin, J.S. Schuman, W.G. Stinson, W. Chang, M.R. Hee, T. Flotte, K. Gregory, C.A. Puliafito, and J.G. Fujimoto. "Optical Coherence Tomography." Science, 254, 1178-1181 (1991).

W. Drexler, U. Morgner, F.X. Kartner, C. Pitris, S.A. Boppart, X.D. Li, E.P. Ippen, and J.G. Fujimoto. "In vivo ultrahigh-resolution optical coherence tomography." Optics Letters, 24, 1221-1223 (1999).

M. Ohmi, T. Kurata, M. Sekimoto, and M. Haruna. "Quasi in-focus optical coherence tomography." Japanese Journal of Applied Physics Part 1—Regular Papers Short Notes & Review Papers, 43, 845-849 (2004).

Z.P. Chen, T.E. Milner, D. Dave, and J.S. Nelson, "Optical Doppler tomographic imaging of fluid flow velocity in highly scattering media." Optics Letters, 22, 64-66 (1997).

J.M. Schmitt, S.L. Lee, and K.M. Yung. "An optical coherence microscope with enhanced resolving power in thick tissue." Optics Communications, 142, 203-207 (1997).

F. Lexer, C.K. Hitzenberger, W. Drexler, S. Molebny, H. Sattmann, M. Sticker, and A.F. Fercher. "Dynamic coherent focus OCT with depth-independent transversal resolution." Journal of Modern Optics, 46, 541-553 (1999).

B. Qi, A.P. Himmer, L.M. Gordon, X.D.V. Yang, L.D. Dickensheets, and I.A. Vitkin, "Dynamic focus control in high-speed optical coherence tomography based on a microelectromechanical mirror." Optics Communications, 232, 123-128 (2004).

V.X.D. Yang, N. Munce, J. Pekar, M.L. Gordon, S. Lo, N.E. Marcon, B.C. Wilson, and I.A. Vitkin, "Micromachined array tip for multifocus fiber-based optical coherence tomography." Optics Letters, 29, 1754-1756 (2004).

X.M. Liu, M.J. Cobb, Y.C. Chen, M.B. Kimmey, and X.D. Li. "Rapid-scanning forward-imaging miniature endoscope for real-time optical coherence tomography." Optics Letters, 29, 1763-1765 (2004).

A.G. Podoleanu, J.A. Rogers, and D.A. Jackson. "Three dimensional OCT images from retina and skin." Optics Express, 7, 292-298 (2000).

Y.C. Chen and X.D. Li. "Dispersion management up to the third order for real-time optical coherence tomography involving a phase or frequency modulator." Optics Express, 12, 5968-5978 (2004).

G.J. Tearney, M.E. Brezinski, J.F. Southern, B.E. Bouma, M.R. Hee, and J.G. Fujimoto. "Determination of the Refractive-Index of Highly Scattering Human Tissue by Optical Coherence Tomography." Optics Letters, 20, 2258-2260 (1995).

* cited by examiner

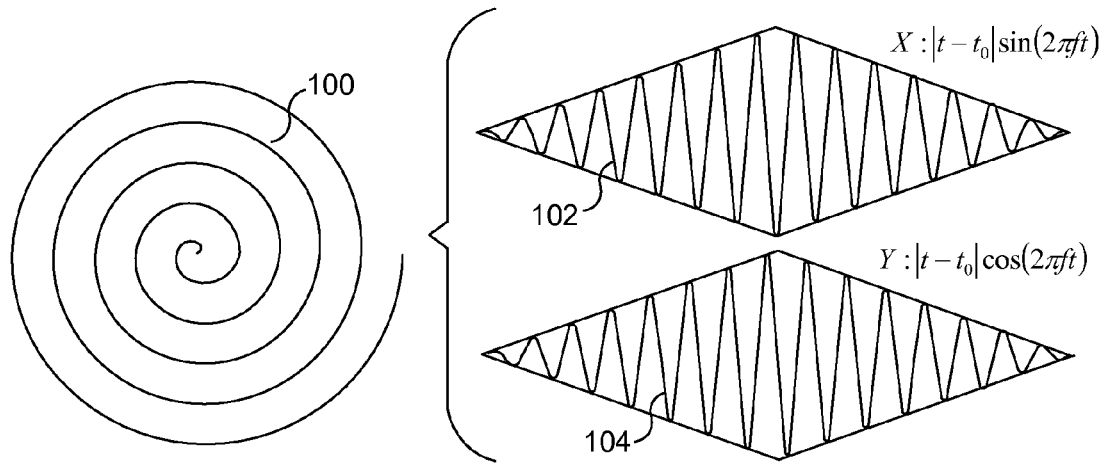
FIG. 10   FIG. 11
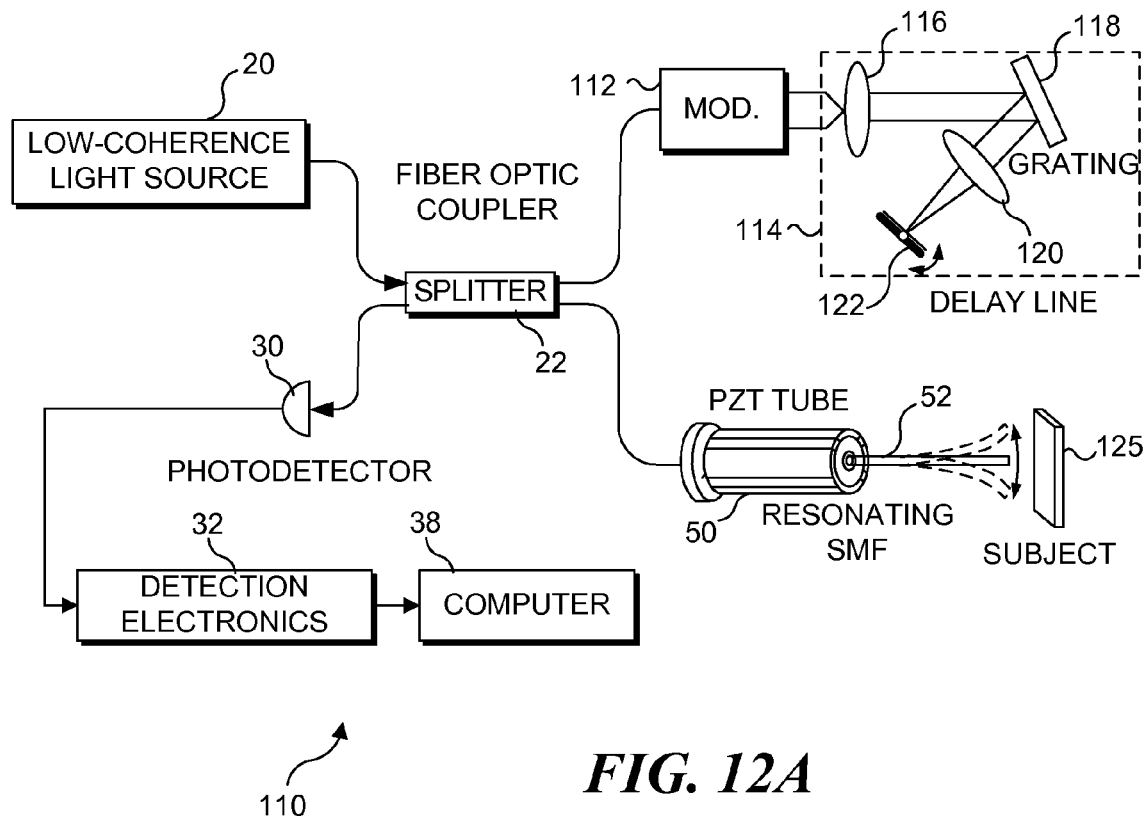
FIG. 12A

OPTICAL FIBER SCANNER FOR PERFORMING MULTIMODAL OPTICAL IMAGING

RELATED APPLICATION

This application is a continuation-in-part of a U.S. patent application Ser. No. 09/850,594, filed on May 7, 2001 now U.S. Pat. No. 6,975,898, the benefit of the filing date of which is hereby claimed under 35 U.S.C. § 120.

GOVERNMENT RIGHTS

This invention has been funded at least in part through grants from the National Institutes of Health (NIH) under Federal Reporting note 1 R21 CA96633-01 and Federal Reporting note 1 R21 CA094303-01A1 and the U.S. government may have certain rights in this invention.

FIELD OF THE INVENTION

The present invention is generally directed to a method and optical fiber scanner that is used for either confocal imaging, optical coherence tomography (OCT), or multiphoton excitation imaging (including multiphoton fluorescence and harmonic generation imaging), and more specifically, to a method and optical fiber scanner in which a distal portion of the optical fiber scanner is moved in a desired pattern to scan transversely before shifting focus to a different depth.

BACKGROUND OF THE INVENTION

Cancer is a leading cause of death in the United States. Each year, more than a million U.S. residents are diagnosed with cancer; however, recent statistics indicate that for the first time in five decades, cancer mortality is declining. Advances in cancer diagnostic techniques involving imaging technology is one of the key factors contributing to this decrease. Currently, the standard procedure for cancer diagnosis requires a biopsy of a suspect site, followed by tissue histology. Unfortunately, biopsy is an invasive procedure and often results in unacceptably high rates of false negative diagnoses because of random sampling errors, particularly when the area of interest is small (as in cases of early cancers). Thus, it would be preferable to use a different approach for cancer screening and early cancer detection that provides more accurate results and is less invasive.

More than 70% of all cancers originate in the epithelial lining of internal organs. Some of the more common examples include cancers of the esophagus, colon, bladder, and lung that can develop over a period of several years and are characterized by changes in tissue and cellular morphology before invasion and metastasis occur. While x-rays, positron emission tomography (PET), magnetic resonance imaging (MRI), ultrasound, and surface tissue endoscopy have all played significant roles in the detection of macroscopic abnormalities (e.g., large tumors and strictures), physicians are still challenged by their limited ability to detect and examine microscopic changes in early-stage neoplasia in vivo, using current clinical imaging technologies, which often have insufficient image resolution to provide the information required.

Scanning confocal microscopy, OCT, and multiphoton microscopy (MPM) are three non-invasive optical technologies that are capable of imaging tissue microstructures at or near cellular resolution (~0.5-10 µm) in vivo. These technologies have the potential for performing "optical biopsy" at resolutions near those of conventional histological techniques, but without the need for tissue removal. All three techniques require mechanisms that deliver, focus, scan, and collect a single mode optical beam. Conventional microscopes equipped with galvanometer or rotating polygon mirrors can perform this scanning task when imaging biological samples or tissues that are easily accessed externally, outside a patient's body. Yet, such devices are typically too bulky and are thus often the limiting factor in imaging probe miniaturization. Imaging internal organs requires extreme miniaturization of the scanning apparatus. Although it is possible to deliver an optical beam to internal organs using a single mode optical fiber, the integration of beam scanning, focusing, and collection using an endoscope only a few millimeters in diameter is a major engineering challenge that has not successfully been solved in the prior art.

A further challenge is the need for a focus-tracking mechanism that can maintain a high transverse resolution at varying depths, in particular when the focused spot sizes are small. For example, conventional confocal microscopy is a well-established technique that can image tissue specimens and living tissues at cellular resolution, and most in vivo human imaging using confocal microscopy focuses on tissues that are easily accessed externally, such as the eyes and skin. Although attempts have been made to integrate fiber-optic imaging bundles with scanning confocal microscopy for imaging internal organs, wherein the fiber-optic bundle relays tissue images from internal organs to a conventional scanning confocal microscope outside the human body, the resulting resolution is sub-optimal and generally unsatisfactory for most purposes. The lower resolution is primarily due to cross-talk between fibers and limited fiber packing density.

Recently, micro-electrical-mechanical-system (MEMS) scanners have undergone intensive investigation, and it appears that it may be possible to use MEMS scanners to perform beam scanning endoscopically. Yet, a MEMS-scanner-based endoscope is still relatively large (e.g., ~5-8 mm in diameter) because of the required supporting substrate, electrodes, and packaging. In addition, MEMS scanners may also introduce wave front deformation to the imaging beam, since MEMS mirrors are thin and tend to warp during scanning.

Perhaps a more promising approach in endoscopic beam scanning is to scan an optical fiber tip to image tissue at a desired internal location within a patient's body. An optical fiber can be mounted on a metal base plate (e.g., a tuning fork) and actuated by electromagnetic oscillation. An imaging device using this scanning scheme with a diameter of ~3-6 mm has been demonstrated. Further size reduction is difficult, as a result of limitations imposed by the size of the electromagnetic actuator. A similar approach has been reported in which an optical fiber attached to an electric coil is actuated by a stationary magnet when an AC current is applied to the coil. This optical fiber scanner has a smaller diameter, ~3 mm, and can achieve a 2-mm transverse scan. Yet, the scanning speed is severely limited to a few transverse scans per second.

Providing suitable miniature imaging optics is another important consideration for confocal endoscopy. Elegant miniature optics using a graded index (GRIN) lens and a compound sol-gel lens have been reported in the prior art. The magnification achieved by such a device is ~4×-8×, corresponding to a focal spot size of about 20-40 µm (i.e., a fiber mode field diameter of 5 µm, multiplied by the magnification factor). Although GRIN lenses can be readily implemented in the scanning fiber endoscope, it is well known that GRIN lenses can cause chromatic aberrations. Yet, this problem can likely be resolved by developing miniature optics with a lower magnification as well as minimal optical aberration (spherical and chromatic).

OCT is an emerging non-invasive technology that can perform cross-sectional imaging of tissue microstructures in vivo and in real-time. OCT is analogous to ultrasound in imaging applications, except that it uses low-coherence light rather than acoustic waves to image tissues. The echo delay time or the depth of light backscattered from the tissue is measured using a technique called low coherence interferometry. The heterodyne detection gives OCT extremely high detection sensitivity in excess of 100 dB, corresponding to the detection of backscattered optical signals of 1 part in $10^{10}$. FIG. 1 (Prior Art) schematically illustrates a conventional OCT system. This system includes a Michelson interferometer that uses a low coherence light source 20. The light source is coupled to an OCT probe 24 in the sample arm and to a reference arm 28 through an optic fiber coupler or beam splitter 22. The sample arm delivers an optical beam from the light source to tissue 26 and collects the backscattered light. The reference arm performs depth scanning by using a translating retro-reflective mirror or a phase-controlled scanning delay line (not separately shown). The backscattered intensity versus depth forms an axial scan. Two- or three-dimensional data sets formed by multiple adjacent axial scans are obtained by scanning the OCT beam along the transverse direction after each axial scan. A photodetector 30 produces a corresponding analog signal comprising the data set. The analog signal is processed by detection electronics module 32, which produces corresponding digital data. The resulting data set can be displayed using a computer 38, as a false-color or gray-scale map, to form a cross-sectional OCT image.

Unlike confocal microscopy, the transverse and axial resolutions of OCT are determined independently. The axial resolution, $\Delta z$, is given by the coherence length of the light source and is inversely proportional to the source spectrum bandwidth $\Delta \lambda$, i.e., $\Delta z = (2 \ln 2/\pi)(\lambda_0^2/\Delta \lambda)$, where $\lambda_0$ is the source center wavelength. The transverse resolution, $\Delta x$, is determined by the transverse focused spot size, in a manner similar to that in conventional microscopy, i.e., $\Delta x = (2\lambda/\pi)/N.A.$, where $N.A. = d/2f$, d is the beam spot size on the objective lens, and f is the focal length of the objective.

It is well known that an increase in the transverse resolution reduces the depth of focus quadratically, i.e., $b = (\pi \Delta x^2)/2\lambda$, where b is the depth of focus (or the confocal parameter). For example, the depth of focus decreases from ~200 μm to ~50 μm when the transverse resolution increases from 10 μm to 5 μm. Conventional OCT has a low transverse resolution between 20 μm and 40 μm. Thus, focus tracking is not necessary for low resolution OCT. However, low transverse resolution degrades image contrast. Even with coherence gating along the axial direction, photons that are backscattered within the focal spot size by different scatterers (e.g., by cells or cell organelles) will likely be simultaneously detected and averaged, causing loss of contrast. Therefore, a high transverse resolution is needed. When high N.A. optics are utilized to achieve a high transverse resolution, focus tracking is clearly required. As discussed above, conventional OCT imaging acquires one axial scan followed by other axial scans, each at a different transverse location. A 2-3 mm axial scan generally takes less than 2 ms during real-time imaging, requiring focus tracking at a velocity of ~4-6 meters per second, which is extremely difficult to achieve in a compact scanning device. FIG. 2 illustrates the rapid depth scanning of tissue 42 by an incident beam 40, and the relatively slow transverse scans that are used. In this conventional technique for OCT scanning, focus tracking means that the focus point is rapidly tracked at each different transverse location before moving to the next transverse location, which is very challenging to achieve.

The core of a single mode optical fiber in an OCT imaging system will function optically much as a pinhole does in a confocal microscope. Thus, a fiber-optic OCT system can also be employed as a confocal microscope, with the added benefit that OCT provides superb axial resolution by using coherence gating. Reportedly, a confocal microscope equipped with low coherence gating (resulting in a device known as an optical coherence microscope) improves the imaging depth by a factor of more than 2, compared to conventional confocal microscopy. A unified imaging modality is expected to have an enhanced resolution (both transverse and axial) and should enable imaging tissue microstructures at or near cellular levels.

Clearly, what is needed is an approach that enables forward-directed OCT scanning or confocal imaging to be carried out without the need for focus tracking at high velocities that are difficult to achieve. An OCT scanning system and technique would be desirable that can be implemented using a scanner sufficiently compact to be readily inserted within a patient's body with minimal invasive consequences. The scanner should produce high resolution scans and provide detailed information that can be evaluated by medical personnel to determine the condition of the tissue being imaged. Prior art advances in OCT and confocal imaging have not yet achieved this goal.

There is another important related imaging paradigm. Multiphoton microscopy (MPM) has become a powerful tool for detailing subcellular structures and events. This technology relies on two or more long wavelength photons arriving "simultaneously" at a fluorophore, where the energies add and induce an electronic transition that is normally excited by a single short wavelength photon. Among the many advantages over single photon excitation, the nonlinear excitation process of MPM is restricted to a submicron-size volume at the focus of the light beam, providing a superb resolution. Unlike OCT and confocal microscopy, MPM is sensitive to biochemical information, including cellular NAD(P)H, flavin, retinal condition, etc. Recent in vivo animal model studies have demonstrated that MPM is an enabling technology for assessing tumor pathophysiology and differentiating metastatic from non-metastatic tumors. A variation of MPM may become useful for imaging anisotropic molecules and biological structures without the requirement of fluorescence; this variation employs the mechanism of harmonic generation such as second harmonic generation (SHG) or higher harmonic generation. For example, the SHG signal from collagen is typically at one-half the two-photon excitation wavelength in the near infrared. Studies have also shown the feasibility of MPM for in vivo imaging of human skin with cellular resolution.

Recently, active research has been devoted to endoscopic MPM. One major technical difficulty is the temporal broadening of femtosecond pulses through optical fibers due to the group velocity dispersion (GVD) and self-phase modulation (SPM), which results in a power-law decrease of multiphoton excitation efficiency. Preliminary studies have suggested that this problem could be potentially overcome using large core multimode fibers, novel microstructured or photonic bandgap optical fibers. It would thus also be desirable to develop endoscopic applications of MPM using an optical fiber scanner.

SUMMARY OF THE INVENTION

In accordance with the present invention, a method is defined for using an optical fiber scanner for carrying out rapid scanning during forward imaging of a subject, such as a tissue site in a patient's body. Depending upon its configuration, the optical fiber scanner can be used to carry out either OCT, confocal, or multiphoton excitation imaging of the subject. The method includes the steps of advancing the optical fiber scanner to a position adjacent to the subject. A distal portion of the optical fiber scanner is actuated to rapidly move generally within a plane in a desired scanning pattern. After scanning at a current depth in the subject, a focal point of the scanning optical fiber imager is moved generally in a direction orthogonal to the plane in which the scanning occurred, to scan at a different depth. The scanning at a given depth followed by a movement of the focal point to a different depth and scanning again is repeated for each depth to be scanned.

The step of actuating can cause the distal portion of the optical fiber scanner to move back and forth generally laterally relative to a longitudinal axis of the optical fiber scanner (i.e., in a desired scanning pattern comprising a one-dimensional, linear path), or can cause it to move in a two-dimensional, area scanning path comprising the desired scanning pattern. For example, the desired scanning pattern can be a spiral pattern or a propeller scan pattern.

When carrying out OCT, the method further comprises the step of employing an electro-optic or acousto-optic modulator in either a reference arm coupled to the optical fiber scanner or in a sample arm. The use of a modulator is well known in the art of OCT and is therefore not described in detail in regard to the present invention.

Also, the step of actuating the distal portion preferably comprises the step of driving the distal portion of the optical fiber scanner to vibrate at either its resonant frequency or near its resonant frequency. In this step, the distal portion of the optical fiber is preferably driven to move in one direction, or in two generally orthogonal directions. The directions in which the distal portion of the optical fiber moves are generally orthogonal to a longitudinal axis of the optical fiber scanner.

The focal point of the optical fiber scanner is moved to focus on a different depth in the subject at a substantially slower rate than the distal portion is actuated to scan transversely in the desired pattern. The focal point of the optical fiber scanner is thus moved longitudinally in a stepwise or continuous manner, scanning transversely at each different depth desired before moving to the next of the plurality of different depths, or as the depth varies continuously.

One embodiment includes the step of focusing light passing through a distal end of the optical fiber scanner using a lens that is optically linked thereto. The lens that is optically linked to the distal end of the optical fiber scanner preferably comprises either a graded index (GRIN) type lens or a miniature compound achromatic lens.

Light passing through a distal end of the optical fiber scanner is collected and focused using a lens that is longitudinally movable relative to a distal end of an optical fiber. Changing the relative position of this lens adjusts the focal point of the optical fiber scanner at a desired depth in the subject.

The step of moving the focal point of the optical fiber scanner can be done in one of several different ways, including actuating an elastomeric polymer that changes length in response to an electric potential, changing a focus of a variable focus fluid lens in response to an electric potential, driving a motor to rotate a shaft that shifts the focal point longitudinally, applying either a hydraulic or pneumatic pressure to overcome a spring tension and thereby shifts the focus, or controlling a pressure applied to vary a separation between tissue at a site and the distal portion of the optical fiber scanner. Each of these various approaches can thus shift the focal point longitudinally to enable transverse scanning at each different depth. Another embodiment includes a beamsplitter that directs a portion of the light from the light source transversely relative to a longitudinal axis of the optical fiber scanner, and a deformable membrane mirror, which shifts the disposition of the focal point of the optical fiber scanner in response to an electric potential applied to the deformable membrane mirror, causing the disposition of the focal point to change in the direction in which the portion of the light is penetrating into the subject.

Preferably either an angled bevel is created on a distal end of an optical fiber through which light is conveyed in the optical fiber scanner, or an anti-reflection coating is applied to one or more possibly reflective surfaces, to substantially reduce back reflection.

Typically, the optical fiber scanner will be advanced to a site in a patient's body by delivering the optical fiber scanner to the site with an endoscope.

Another aspect of the present invention is directed to an optical fiber scanner adapted for use in carrying out a rapid scan during forward imaging of a subject. Again, the optical fiber scanner can be used either for OCT, confocal, or multiphoton excitation imaging of the subject. The optical fiber scanner includes a light source that produces light, and an optical fiber having a proximal end and a distal end. The light source is optically coupled to the proximal end of the optical fiber, and the distal end of the optical fiber is adapted to be positioned adjacent to subject. A scanning actuator is disposed adjacent to the distal end of the optical fiber and vibrates a distal portion of the optical fiber, causing light produced by the light source that is conveyed through the optical fiber to scan a region of interest in a desired scanning pattern. A focusing lens is also disposed proximate to the distal end of the optical fiber. A focal point displacer moves the focusing lens generally longitudinally to change a disposition of a focal point of the optical fiber scanner, in order to scan at a different depth, after the scanning actuator has completed scanning at a previous depth. A light detector responds to light conveyed through the optical fiber that was reflected from the subject, producing a signal. Generally, other aspects and functions performed by the optical fiber scanner are consistent with the steps of the method discussed above.

The present invention also encompasses endoscopic applications of MPM, which are achieved by combining an optical fiber scanner with high N.A. miniature optics, and a mechanism for maintaining the temporal profile of a short pulse that is suitable for MPM. In accord with this invention, a scanning, fiber-optic multiphoton fluorescence imaging system includes a short-pulse laser (e.g., a femtosecond Ti:Sapphire laser), a pre-chirping unit (potentially needed), a beamsplitter, the fiber-optic scanning probe (or endoscope), an optical filter (to remove the excitation light), a light detector, detection electronics and an image processing/display unit (e.g., a computer).

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 10 schematically illustrates a spiral scan pattern that is useful in scanning at each depth, in accord with the present invention;

FIG. 11 illustrates the triangularly modulated sine and cosine signals that drive a cantilevered optical fiber to vibrate relative to X and Y orthogonal axes in the optical fiber scanner of the present invention;

FIG. 12A is a schematic block diagram of an OCT system in accord with the present invention;

DESCRIPTION OF THE PREFERRED EMBODIMENTS

Figure 1:
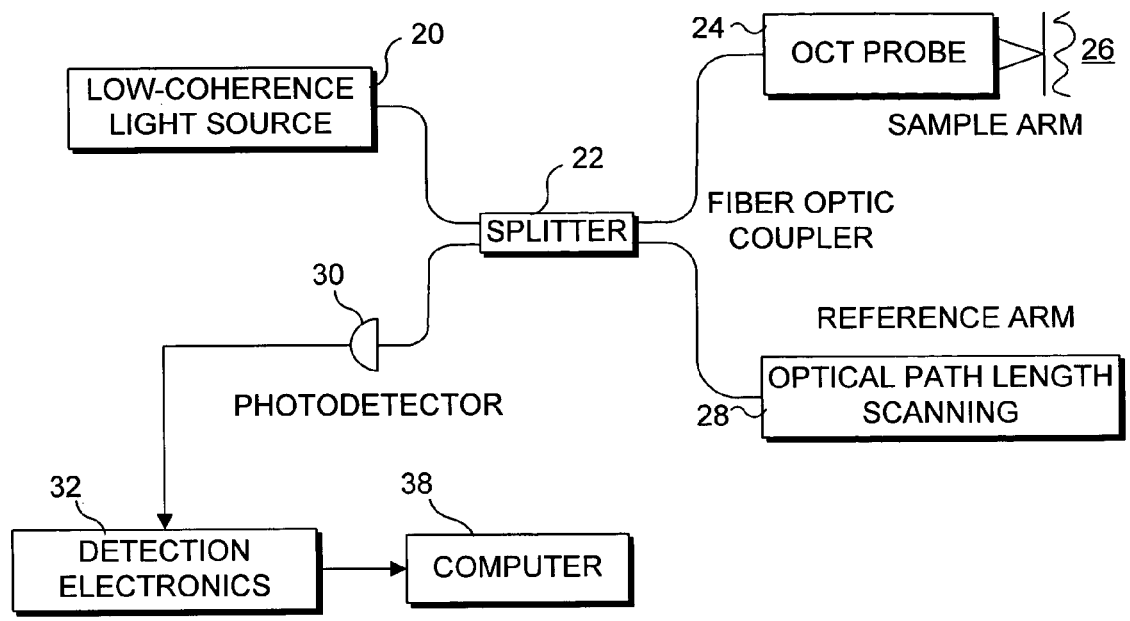
FIG. 1 (Prior Art) is a schematic block diagram of a typical OCT system.
Figure 2:
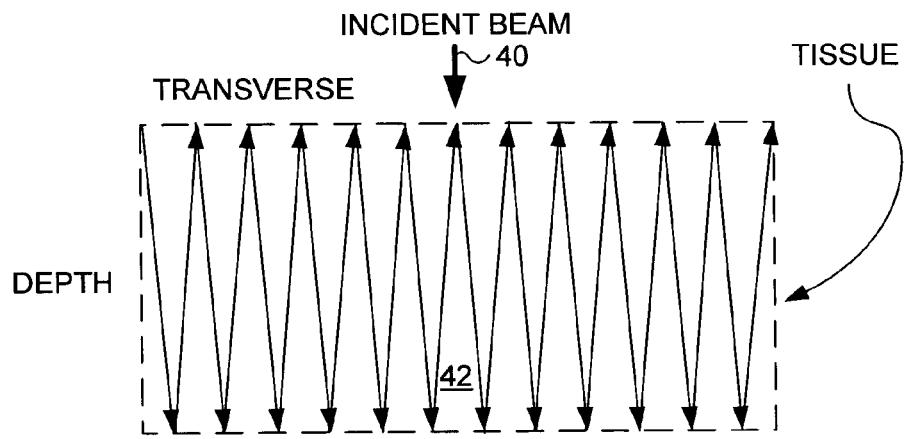
FIG. 2 (Prior Art) is a schematic representation of the scanning pattern of a conventional OCT system, which rapidly scans at different depths, moves transversely to a different point, and then again rapidly scans at different depths.
Figure 3:
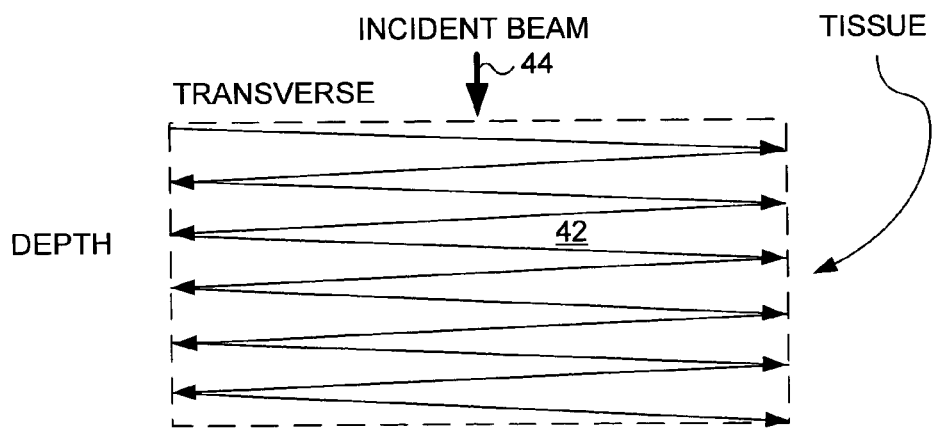
FIG. 3 is a schematic representation of the scanning pattern of the present invention, which rapidly scans transversely at a given depth, while slowly moving to a different depth, and again rapidly scans transversely.

A key advantage of the present invention over other prior art OCT scanning systems is that the depth focus tracking is varied relatively slowly compared to the transverse scanning speed. Unlike prior art OCT scanning systems that employ the scanning procedure illustrated in FIG. 2, the present invention scans transversely relatively rapidly at a current depth, then moves the focus point to a different depth and repeats the rapid transverse scan at the new depth. FIG. 3 illustrates this scanning procedure in tissue 42 for an incident beam 44 that scans transversely in each of a plurality of different depths before shifting to a new different depth. Accordingly, in the present invention, it is not necessary to rapidly track the focus point in depth for each different transverse position. Instead, the transverse scanning is done much more rapidly, compared to the rate at which the focus point is shifted, and it completes a transverse scan at each of successively different depths or within the thickness of the slice, before shifting to the next depth. The present invention is ideally suited for this scanning technique, since it includes a cantilevered optical fiber that is readily driven to scan along a linear path, or two-dimensionally in a desired pattern, such as in a spiral, propeller, Lissajous, or any other two-dimensional scanning pattern.

Figure 4:
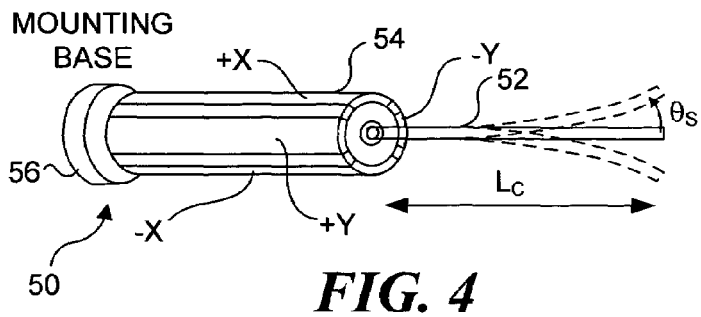
FIG. 4 is a schematic isometric view of an optical fiber scanner for use in the present invention.

An optical fiber scanner 50 that is suitable for use in the present invention is illustrated in FIG. 4. Optical fiber scanner 50 includes a cantilevered optical fiber 52 (which is preferably single mode) that is driven in either one or two (orthogonal) directions by a tubular lead zirconate titanate (PZT) actuator 54 (or using any other suitable piezoelectric or electromagnetic actuator). The PZT actuator is supported by a base 56. Although not shown in this simplified drawing, a GRIN lens or other type of rod lens may be fused to the distal end of the cantilevered optical fiber, for focusing light passing through the optical fiber. Pairs of electrodes (one electrode for each of the X and −X, and Y and −Y axes, each electrode being disposed on a different quadrant) are included on the PZT actuator for coupling to a suitable drive signal. When these electrodes are energized with appropriate drive signal(s), the PZT actuator causes cantilevered optical fiber 52 to vibrate and thus scan in a desired pattern. For example, when sine and cosine waves have the waveforms shown in FIG. 11 are respectively applied to the two pairs of electrodes, the resulting scan will be a spiral, as shown in FIG. 10. A circular scan is produced when the horizontal (X) and vertical (Y) resonance vibrations are at the same frequency and equal in amplitude, but 90° out of phase. The space-filling spiral scan of FIG. 10 is generated when both amplitudes are modulated in a triangle pattern, while the relative phase is kept constant. Each half cycle of the triangle modulation in FIG. 11 is a frame, and the rising half cycle of the triangular modulation generates an opening spiral pattern, while the falling half cycle generates a closing spiral pattern. For imaging at a constant sampling rate, the central portion of the spiral scan field is over sampled and the periphery is under sampled. Interpolation along the annulus can be performed to fill in the pixels that are not sampled, and decimation can be applied to the over sampled pixels. Spiral scanning has the advantage of using only a single tubular PZT to generate the 2-D spiral scans from within a small cylindrical enclosure.

As the sinusoidal wave frequency applied to drive the cantilevered optical fiber more closely approaches the mechanical resonance frequency of the optical fiber, the transverse displacement of the cantilevered optical fiber will approach a maximum. The resonant frequency of a cantilevered optical fiber with a round cross section is given by:

$$f = \frac{\beta}{4\pi}\sqrt{\frac{E}{\rho}}\left(\frac{R}{L^2}\right) \quad (1)$$

where L and R are the length and radius of the cantilevered optical fiber, respectively, E and $\rho$ are respectively Young's modulus and the mass density of the optical fiber, and $\beta$ is a constant determined by the vibration mode number and boundary conditions of the cantilever. In an initial prototype of the present invention, the fundamental vibration mode was used, and $\beta \approx 3.52$.

In this initial prototype, a 7.2 mm-long PZT actuator 54 having a 1.5 mm diameter was used. The proximal end of the PZT tube was adhesively attached to base 56, which had a slightly larger diameter (i.e., 1.8 mm) than the PZT actuator. A thin holder 55 (shown in the photograph of FIG. 5) was attached within the distal end of the PZT actuator to support the cantilevered optical fiber during its vibration (i.e., while pivoting with respect to the center of the holder). The distal tip of the cantilevered optical fiber was cleaved at an 8° angled bevel to reduce the back reflection of light at its junction with the GRIN lens. The measured resonant frequency of single mode cantilevered optical fiber 52, which was about 8.5 mm long, was about 1.4 kHz.

Figure 5:
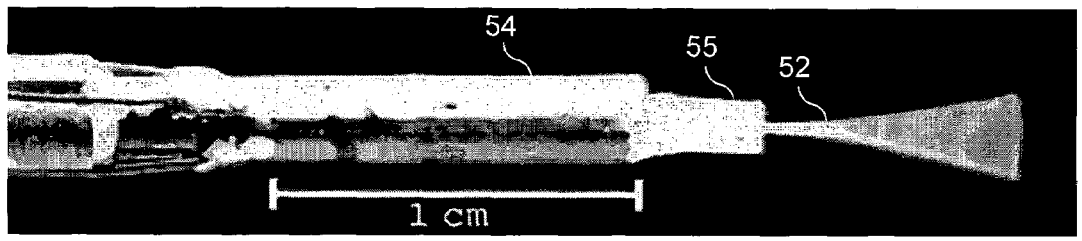
FIG. 5 is a photograph of a prototype optical fiber scanner generally like that of FIG. 4.

FIG. 5 is a photograph of resonating cantilevered optical fiber 52 in the first mode of vibratory resonance. (Several of the elements discussed in this paragraph in regard to the optical fiber scanner are not shown in FIG. 4 or 5, but are shown and discussed in regard to other embodiments, such as that of FIG. 8.) The tip of the scanning optical fiber was imaged onto a target tissue (not shown) with a GRIN lens (not separately identified) having a 0.25-pitch length (NA=0.46), and a 1.8-mm diameter. The cantilevered optical fiber and GRIN lens were encased within a separate cap (not shown) made of a 13-gauge stainless hypodermic tube, which snugly slid over base 56. The proximal end of the GRIN lens (i.e., the end facing the distal tip of the cantilevered optical fiber) was polished at an 8° angled bevel to match the cleaved 8° angled bevel on the distal tip of the cantilevered optical fiber. The working-distance and the focused spot size are adjustable in this prototype by changing the object distance between the tip of cantilevered optical fiber 52 and the GRIN lens. In the prototype, a 1.5 mm object distance and a 3.5 mm working distance were chosen. The measured transverse resolution was 16 µm, with a confocal parameter of 0.32 mm. The lateral scanning range of the imaging beam on the focal plane is equal to the scanning range of the distal tip of the cantilevered optical fiber multiplied by the magnification of the GRIN lens, which is proportional to the amplitude of the applied sinusoidal PZT drive signals. For instance, a 2.5 mm lateral scanning range can be readily achieved when both pairs of electrodes are actuated with a PZT drive voltage of ±30 volts (60 volts peak-to-peak). The drive current is very small (<100 µA) due to the high capacitive impedance of the PZT electrodes. The entire endoscope was encased within a TEFLON™ plastic tube (not shown), providing extra insulation and protection. The overall diameter of the resulting scanning endoscope, including the hypodermic tube, was 2.4 mm, and the length of the rigid portion was 32 mm.

For use in endoscopic scanning for OCT, an optical fiber scanner can be driven to resonate (or near its resonance frequency) in either its first or second mode. The resonant frequency can be tuned by choosing the length and the diameter of the fiber, and by changing the optical fiber mass distribution through chemical etching processes. These processes can be precisely controlled, ensuring the modified mass distribution has a cylindrical symmetry in order to minimize any potential instability of the optical fiber tip.

Figure 6:
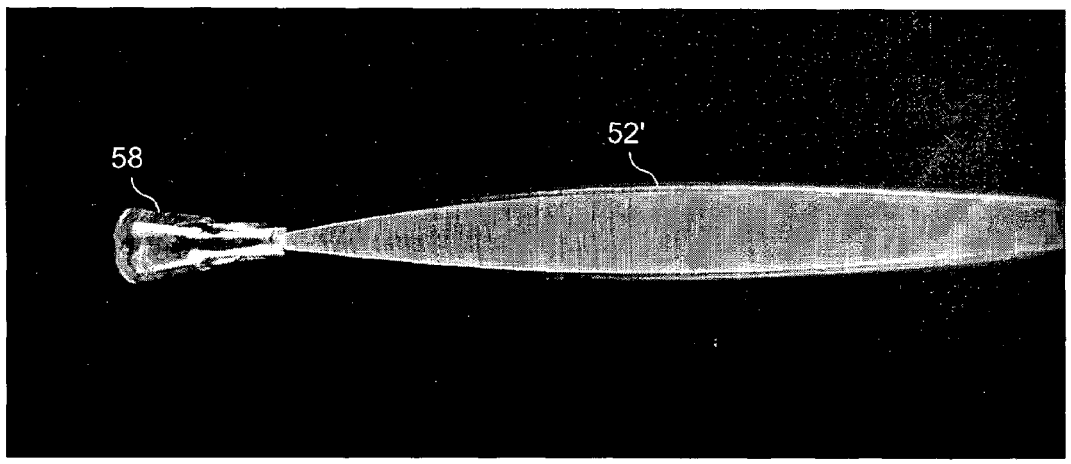
FIG. 6 is a photograph of a vibrating optical fiber that includes a distal lens for focusing and providing added mass at the distal tip of a cantilevered optical fiber.
Figure 7:
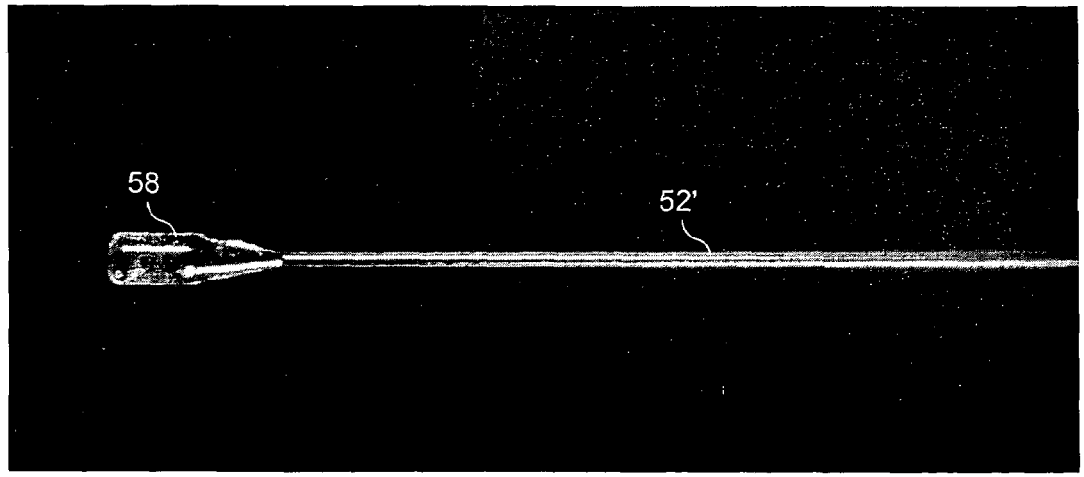
FIG. 7 is a photograph of the optical fiber and distal lens of FIG. 6, when not being vibrated.

Preferably, the first mode is used for a simplified optical fiber scanner with no fused microlens, while the second mode of resonance is used when the fiber scanner has a fused microlens (e.g., a rod lens—either GRIN and/or refractive and/or diffractive surface). The first mode optical fiber scanner (i.e., the scanner shown in FIGS. 4 and 5) moves the effective point source in an object plane and the more distal optical system (shown in FIGS. 8 and 13) focuses this light at the image plane in tissue. Although more complicated to manufacture, the second mode optical fiber scanner with fused microlens (shown in FIGS. 6 and 7) creates a scanned optical beam from near the second vibratory node allowing a simpler lens system distally (shown in FIGS. 14A-14C). A microlens fused to the distal tip of the fiber scanner allows for a reduced number of lenses distally, reducing the size of the optical system. Much of the role of the distal optical system in the optical fiber scanner having the microlens is to minimize lens aberrations and to be able to change axial focal depth while achieving the highest resolution and field of view in the smallest package.

Figure 14A:
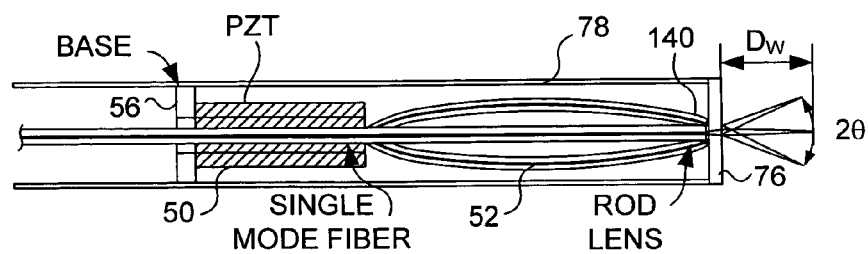
FIG. 14A is a schematic cut-away view of an optical fiber scanner that includes a fused microlens.
Figure 14B:
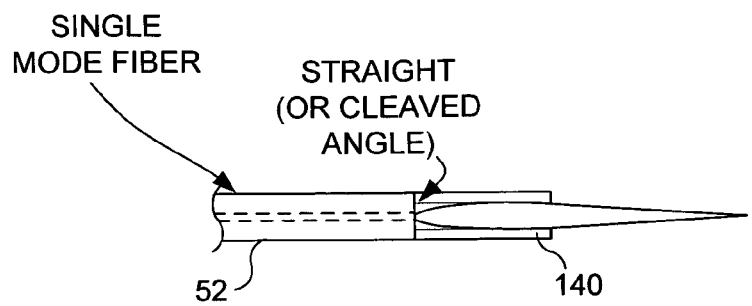
FIG. 14B is an enlarged view of the distal end of a single mode optical fiber with a rod GRIN lens optically linked thereto.
Figure 14C:
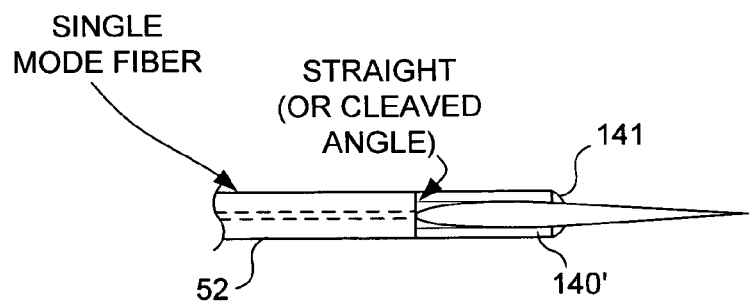
FIG. 14C is an enlarged view of the distal end of a single mode optical fiber with a rod refractive lens optically linked thereto.

A rod lens 140 or 140' affixed to the distal end of the cantilevered optical fiber and used to focus the optical beam minimizes the diameter and rigid length of the optical scan system of an endoscope/catheter in which the scanning optical fiber is employed. The proximal portion of the rod lens can have about the same diameter as the cantilevered single-mode optical fiber and is thermally fused with or adhesively attached to the single-mode optical fiber and then precisely cleaved to a pre-determined length (as shown in FIGS. 14B and 14C). When creating a refractive microlens 141 on the distal surface, $CO_2$ laser heating can be used to form convex surface profiles. The integration of the resonant (or near resonant) optical fiber scanner and the fused lens makes the resulting optical lens system more compact, with the primary purpose of the optical lens system being the focus of the scanned optical beam to have minimal lens and chromatic aberrations and to facilitate the focus tracking mechanism. As discussed above, GRIN lenses can suffer chromatic aberrations, and the aberration can be minimized by using specially designed achromatic micro compound lenses.

For the optical fiber scanner that includes a rod microlens, much of the working distance and acquired image resolution is limited by the fused rod lens parameters. The length, diameter, and distal end curvature for refractive microlens 141 are critical (FIG. 14C), while the length, diameter, and refractive index profile and pitch of the GRIN lens is most important in that embodiment (FIG. 14B). Once the working distance $D_w$ is chosen, the transverse beam scanning range for the first resonant mode is given by $\sim 2D_w \tan\theta$, where $\theta$ is the half scan angle of the optical beam distal of the GRIN lens. For a 2 mm working distance and a 45° scan angle, the transverse scanning range can be ~1.7 mm. The single mode optical fiber and the attached rod lens are micro-fabricated to reduce the overall mass and achieve a higher mass load at the tip (similar to the one shown in FIG. 7), such that the second mode will have a stable pivoting point near the tip of the cantilevered optical fiber.

There are two parameters that could potentially limit the overall diameter of the catheter/endoscope: the diameter of the PZT tube and the maximum transverse deviation of the scanning cantilevered optical fiber. For the first mode, the maximum deviation is about $2L_c^* \tan\theta_c$, where $L_c$ is the cantilevered optical fiber length and $\theta_c$ is the half scanning angle of the cantilever tip. For the second mode, the maximum transverse deviation can be estimated by $h=L_c(1-\cos\theta)/\sin\theta$, where $\theta$ is the half scan angle. For $L_c=8$ mm and $\theta=11°$ (these parameters were chosen to minimize bending loss), the maximum deviation is about 1.6 mm for the first mode and about 0.8 mm for the second mode. For a PZT actuator having a diameter of 1.5 mm, the entire catheter/endoscope should have an outer diameter of 1.8 mm or less, permitting its easy passage through a 2.8 mm accessory port of a standard gastrointestinal endoscope (not shown).

The proposed scanning catheter/endoscope design is easy to implement and has several advantages over a conventional OCT catheter/endoscope. Specifically, no rotary joint is needed; the design permits potential focus tracking that is critical for imaging at a high transverse resolution; and, the design can perform either forward imaging or conventional transverse imaging. Forward imaging is more favorable for screening purpose and therefore represents the primary goal of the present invention. Transverse imaging can be achieved by deflecting the beam by 90° using a flat mirror (not shown) placed at an angle of 45° with respect to the longitudinal axis of the catheter/endoscope.

While use of a rod microlens is preferable because it achieves an efficient compact design for an optical fiber scanner that is readily vibrated in the second mode, its simplistic design also creates a curved imaging field with chromatic aberration. Therefore, a simpler fiber scanner without microlens is contemplated when a plurality of discrete lens elements can be included in an OCT or confocal optical fiber scanner for focusing the light beam at high resolution on a flat field. Accordingly, an effort was made to design and develop a miniature compound lens with a low magnification, minimal aberration, and a nearly ideal telecentricity.

Figure 8:
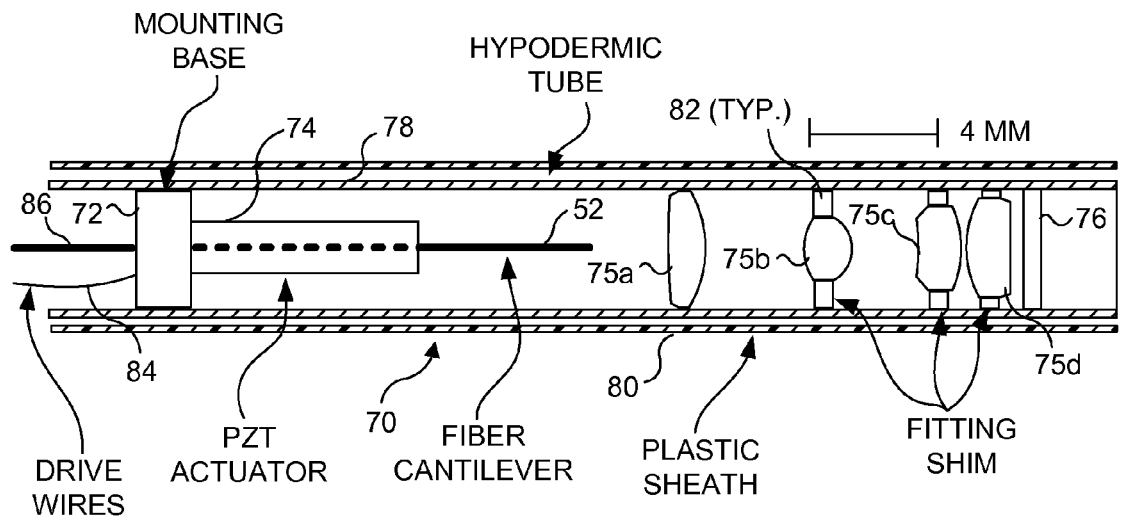
FIG. 8 is a schematic cut-away side elevational view of an embodiment of the present invention using a compound lens system.

A lens system that will likely be included in a design for a forward-looking scanning endoscope 70 is shown in FIG. 8. For use in this device, optical lenses 75a-75d and the cantilevered optical fiber scanner must be small, and care must be taken to insure that they are concentric. All the components are housed in a hypodermic metal tube 78 having an outer diameter of ~5-5.5 mm and a window 76 disposed at the distal end. Precise fitting shims 82 are sandwiched between the hypodermic metal tube and the optical lenses to insure the concentricity. A rigid base 72 of the endoscope and optical fiber scanner is ~3.2 cm long in this exemplary embodiment, and the rest of the endoscope is flexible, including primarily a single mode optical fiber 86 and PZT drive-wires 84. A protective plastic sheath 80 encases the optical fiber and drive wires.

The target scanning frequency of endoscope 70 is about 2.5 kHz, which will generate 5,000 scans per second. If a higher scanning frequency is needed, the cantilever length can be reduced, as indicated by Eq. (1). For instance, the scanning frequency can increase from 2.5 kHz to almost 4 kHz (8,000 scans/s) when the cantilever length is reduced from 5 to 4 mm. To maintain the transverse scanning range, a slight increase in the scanning angle is needed (e.g., from ±12° to ±15°). The miniature optics will then have to be re-optimized to accommodate the increase in the scanning angle.

Back reflection exists at the scanning fiber tip and all the surfaces of the miniature optics. Since the back reflection could overwhelm the optical signal backscattered from the tissue, a broadband anti-reflection coating (substantially non-reflective to light in the spectral band as needed, i.e., anywhere from the visible to near-infrared range, 350-1600 nm) should therefore be applied to all potentially reflective surfaces that might cause such a problem.

Figure 9:
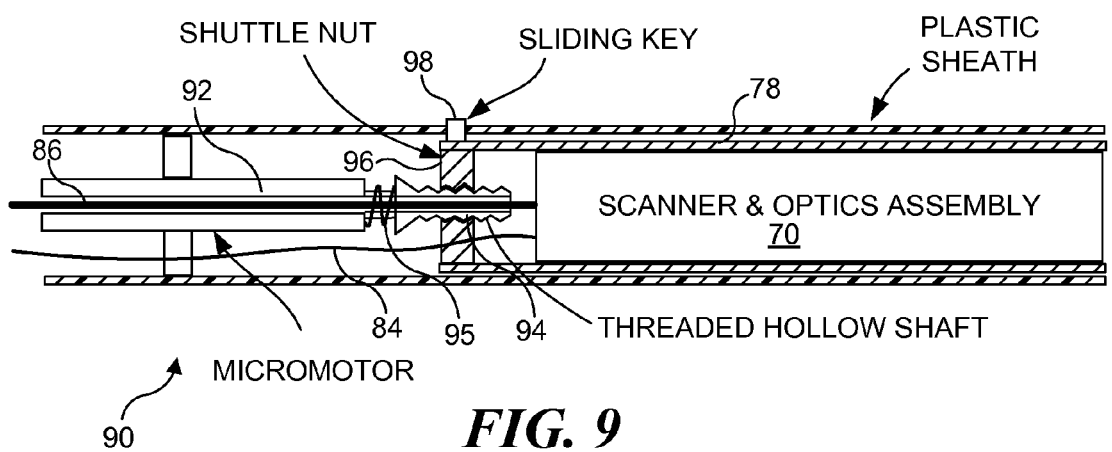
FIG. 9 is a schematic cut-away side elevational view of an embodiment of a longitudinal drive for use in varying the depth of the transverse scan in the present invention.

An important feature of the present invention is the relatively slow change in the position of the focal point in regard to depth in a subject tissue after each transverse scan has been completed, or continuously during the transverse scanning. Accordingly, it is important to provide an acceptable focus-tracking scheme for the scanning miniature endoscope and the other embodiments of the present invention. A first embodiment of a depth focus-tracking system 90 shown in FIG. 9 includes a micromotor 92 disposed adjacent to scanning endoscope 70 to precisely longitudinally translate the scanning endoscope assembly, i.e., the PZT actuator and imaging optics, relative to a subject that is being imaged. The working principle of a micromotor is well known in the art. For this exemplary embodiment, micromotor 92 has a 1.9 mm diameter and rotatably drives a threaded hollow shaft 94. The threaded hollow shaft has an inner diameter of more than 250 µm so that optical fiber 86 can easily pass through the open center bore of the hollow threaded shaft. In addition, the micromotor provides a substantial torque and runs at a controllable high scanning speed, with relatively low power consumption (<10 mW). As the micromotor rotates hollow threaded shaft 94, a shuttle nut 96, which engages the threads on the hollow threaded shaft, is prevented from rotating by a sliding key 98 that slides within a slot (not shown) in the plastic sheath. The shuttle nut is thus forced to move longitudinally as the hollow threaded shaft rotates within the shuttle nut. Shuttle nut 96 is coupled to a proximal end of metal hypodermic tube 78 and thus moves the optical fiber scanner and optics assembly comprising scanning endoscope 70 longitudinally, as well. A helical spring 95 provides a biasing force against hollow threaded shaft 94, transferring the rotation of the micromotor to the hollow threaded shaft, as well as stabilizing the rotation.

Using a shuttle nut 96 having a pitch of 50 threads per inch, each rotation of the hollow threaded shaft translates the endoscope longitudinally by ~500 µm. In order to achieve a real-time depth focus tracking over a 2 mm range at an imaging rate of 10 frames/s, the required micromotor speed is ~2400 rpm. The required rpm for the target focus-tracking speed is thus well within the limits of the micromotor. A lower rpm is sufficient when using a coarse thread pitch (e.g., 30-40 threads/inch). Because the rotation is continuous, a coarse-pitch thread will not adversely impact the accuracy of depth focus tracking.

When the scanning endoscope is longitudinally translated during depth focus tracking, optical fiber 86, which is outside the PZT actuator is "pushed and pulled." However, the total translation is only about 2 mm, and based upon empirical experience, a 2 mm optical fiber longitudinal translation is easily absorbed by a slight bending of the optical fiber within plastic sheath 80, without damaging the optical fiber.

Real-Time Ultrahigh Resolution Cross-Sectional OCT Imaging

Real-time OCT imaging with a miniature endoscope using the image acquisition sequence of FIG. 3 was experimentally demonstrated using an optical fiber scanning OCT system 110, as shown in FIG. 12A. A super luminescent laser diode (SLD) with a 1.29 μm center wavelength and a 31 nm full-width-at-half-maximum (FWHM) spectral bandwidth was employed for low-coherence light source 20. Other advanced low-coherence light sources such as a short-pulse laser and continuum generation in a photonic optical fiber can be used for achieving ultrahigh resolution. For the image acquisition sequence of FIG. 3, an electro-optic modulator 112 was used (alternatively, an acousto-optic modulator can be used) in the reference arm to elevate the Doppler frequency to about 1.5 MHz. The dispersion from the phase modulator crystal (not separately shown) was compensated to a third order by using a grating-based phase-controlled optical delay line 114 that included a lens 116, a grating 118, a lens 120, and a tilting mirror 122. The measured axial resolution after dispersion compensation was approximately 25 μm, which is very close to the ideal value of 24 μm of the low-coherence light source. The slow depth scanning was performed in the phase-controlled optical delay line, and the Doppler frequency shift resulted from the delay line was set to zero by centering the beam at the rotational axis of the tilting mirror.

OCT images of subject tissue 125 were acquired by optical fiber scanning OCT system 110 using the miniature endoscope (represented by optical fiber scanner 50), in accord with the image acquisition sequence shown in FIG. 3. Imaging data were collected with about an 80% data acquisition duty ratio, i.e., within the nearly linear portion of the sinusoidal lateral scan. The non-linearity of the transverse scanning was corrected by software running on computer 38, for the image display. The images were acquired at 6 frames/s, with an image size of 2.0 mm×1.3 mm (1000×466 pixels–transverse× depth).

Fast transverse scanning permits OCT images to be formed by successive transverse scans at different depths in real-time (FIG. 3). In contrast, for the conventional or prior art imaging sequence (FIG. 2), the depth scanning speed is $v_z^c = F \ast Z_d \ast X_{pixel}$, where F is the frame rate, $Z_d$ is the scanning depth, and $X_{pixel}$ is the transverse pixel number (or the number of axial scans) per frame. In the procedure used in the present invention (FIG. 3), where transverse scans are completed before focusing on a different depth (or as the depth is relatively slowly continuously varied), the depth scanning speed is $v_z^r = F \ast Z_d$. Clearly the depth scanning speed used in the present invention is reduced by a factor of $X_{pixel}$, which is on the order of 500. This reduced requirement for depth scanning speed enables the use of a reflective translating mirror in the reference arm of the OCT system, for scanning an ultra broadband light source, making real-time ultrahigh resolution OCT imaging possible. In addition, the reduced depth scanning speed also enables real-time focus tracking.

A 2.5-kHz resonant optical fiber scanner of the present invention produces 5000 transverse scans per second, which corresponds to an imaging rate of 10 frames/s, for an image size of 500 transverse scans. The depth scanning speed is thus approximately 20 mm/s for a 2 mm scanning depth, which is easy to achieve with a translating mirror (or the tilting mirror in the phase controlled optical delay line) in the reference arm of the optical fiber scanner OCT system. When focus tracking is performed, the reflective mirror in the reference arm should not be translated, since the sample arm length is scanned (by focus tracking). Use of a PC based software program that employs Microsoft Corporation's DirectX graphics capabilities should readily enable data acquisition, real-time image display, and hardware synchronization. Transverse and axial point spread functions can be obtained from OCT images for analyzing the resolutions using this system.

Real-Time En Face Imaging:

The same scanning endoscope described above can be used for en face confocal imaging. For this application of the present invention, it will be understood that the imaging is layer-by-layer, and a 3-D image is built up slice-by-slice. To perform 2-D en face scanning that will produce a layer, both the X and Y quadrants of the PZT actuator are preferably driven by the triangle-modulated sinusoidal signals shown in FIG. 11, with the X and Y waveforms 90° out of phase, creating spiral-scanning pattern 100, as shown in FIG. 10. The scanning light beam spirals in and out to produce this pattern. However, other desired scanning patterns can be used in the alternative. The imaging frame rate is twice the triangular modulation frequency. Decimation and interpolation algorithms are employed to compensate for the non-uniform pixel density on the image (i.e., denser at the center and sparser toward the outer periphery). Confocal imaging at different depths is performed using either the depth focus-tracking mechanism of FIG. 9, or that of one of the other embodiments discussed below in regard to FIGS. 13 and 15A-18. The transverse and axial resolution of the confocal imaging endoscope are generally characterized as was explained above for OCT imaging.

Similar to en face confocal imaging, en face OCT imaging is also possible when a modulator is used in the reference arm to introduce a Doppler frequency shift required for heterodyne detection. For en face OCT imaging, the required depth tracking speed is much lower than in the case of the OCT imaging discussed above (in regard to FIG. 3). At an imaging rate of 5 frames/s and assuming the thickness of each image slice is 10 μm, the focus tracking speed is about 50 μm/s. The micromotor of FIG. 13 might not be stable at such a low speed (but this point has not been empirically evaluated). If stability is a problem, one easy solution is to rotate a driver shaft (not shown) threaded into the shuttle nut through a speedometer cable using a galvanometer-driven reduction gear (not shown) disposed at the proximal end of the endoscope.

Figure 12B:
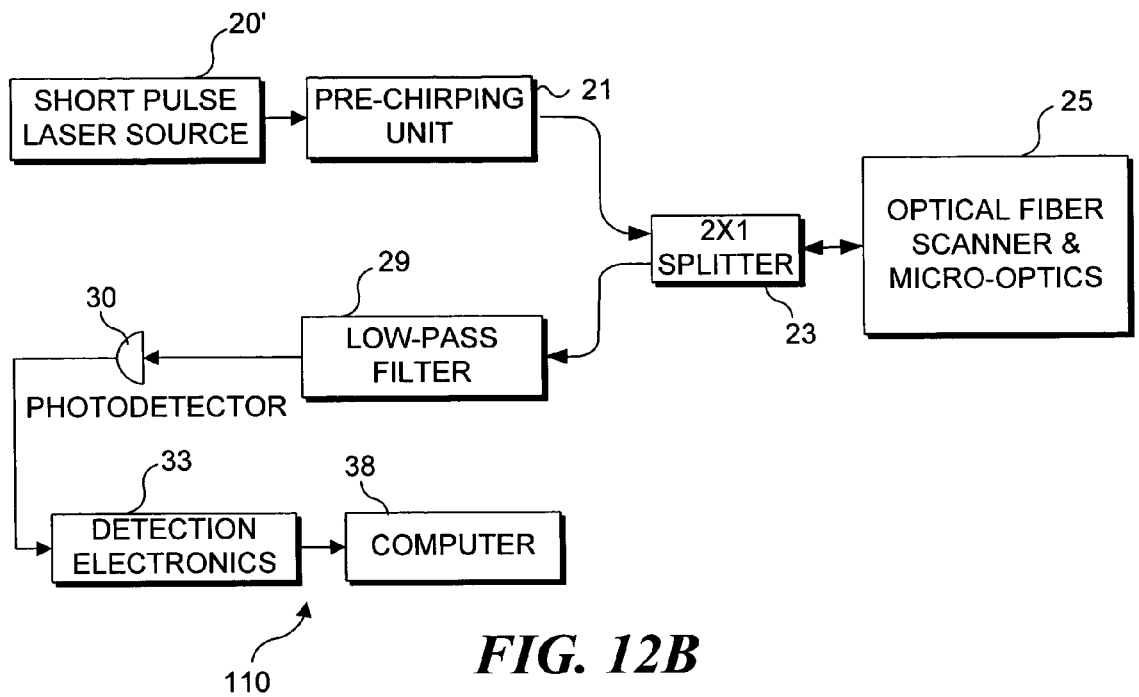
FIG. 12B is a schematic block diagram of a multiphoton excitation imaging system in accord with the present invention.

The basic confocal system design shown in FIG. 12A can be modified for imaging fluorescence, as shown in FIG. 12B. The 2×2 fiber optic splitter (i.e., splitter 22) is replaced with a 2×1 splitter 23, since the reference arm for OCT is not needed. For single photon excitation, a light source with a single wavelength (or wavelengths within a narrow band) is coupled to the optical fiber and the 2×1 splitter, whereas for multiphoton excitation, a short pulse laser source 20' with a desired center wavelength (as well as potentially, a pre-chirping unit 21) is required before coupling to the single mode optical fiber and 2×1 splitter 23, as shown in FIG. 12B. The 2×1 splitter is coupled to an optical fiber scanner and micro-optics module 25. The same optical system can be used for imaging multiphoton excited fluorescence and second harmonic generated light from a sample while using an appropriate low-pass filter 29, the output of which is coupled to photodetector 30. The signal from photodetector 30 is applied to a detection electronics module 33, and its output is processed by computer 38.

After multiphoton excitation, such as two-photon excitation, which generates fluorescence in the target, the challenge is providing an optical system for capturing this signal that spans a large wavelength range between the near infrared (NIR) excitation and typical fluorescence in the visible wavelength range. In FIG. 8, a multi-lens optical system designed for minimizing chromatic aberration across such a wide range of wavelengths is shown. The multi-lens optical system distal to the scanning fiber has been designed for illumination of tissue in one or more NIR wavelengths, while collection of light from the tissue is designed for a pre-selected wavelength range of the fluorescence emission, within a general range that could start in the ultraviolet, using the second harmonic-generated signal (half the excitation wavelength), and extend to longer wavelengths across the visible to NIR fluorescence wavelengths. The lens system in FIG. 8 is designed for NIR multiphoton excitation and fluorescence light detection across a range of light wavelengths of interest, but can also be used for multiple wavelength excitations and multiple ranges of fluorescence emissions with appropriate optical filters. The optics are designed to create a high-power density focal spot in the tissue at the NIR to generate the multiphoton excitation of fluorescence while the same optics are used to collect and convey the visible fluorescence light back to the same optical fiber, collected within the fiber core in a confocal geometry, or within the larger cladding portion in a quasi-confocal geometry.

Alternative Embodiments for Depth Focus Tracking

Figure 13:
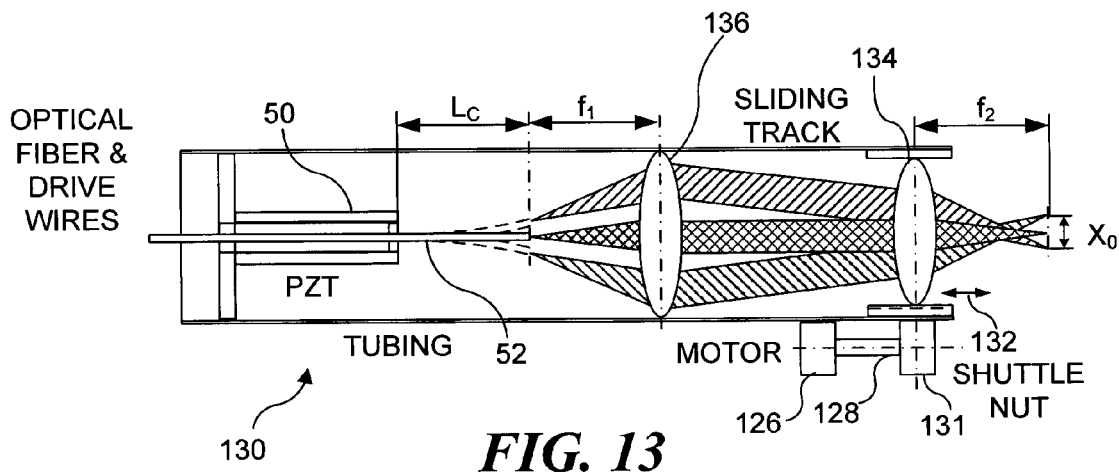
FIG. 13 is a schematic cut-away view of an embodiment that uses a stepper motor to vary the depth of a focal point for each successive transverse scan.

An embodiment 130 for varying depth focus tracking is shown in FIG. 13. Light emitted from cantilevered optical fiber 52 is focused by a lens system that includes a single lens or multiple lenses. FIG. 13 exemplifies a lens system including a lens 136 and a lens 134. Lens 136 is fixed in position relative to the distal end of cantilevered optical fiber 52, while lens 134 moves with its sliding track longitudinally, to shift the position of the focal point in a subject tissue (not shown) in the directions indicated by a double headed arrow 132. To adjust the dept focus tracking, a motor 126 is energized, rotatably driving a threaded shaft 128. Threaded shaft 128 is threaded into a shuttle nut 131, and the shuttle nut is coupled to lens 134, so that when the shuttle nut moves longitudinally, lens 134 is also moved longitudinally. Alternatively, lens 134 can be fixedly mounted in the supporting tube, and lens 136 can be coupled to shuttle nut 131, so that lens 136 is moved longitudinally to shift the depth at which the focus point is located in the subject being scanned.

Figure 15A:
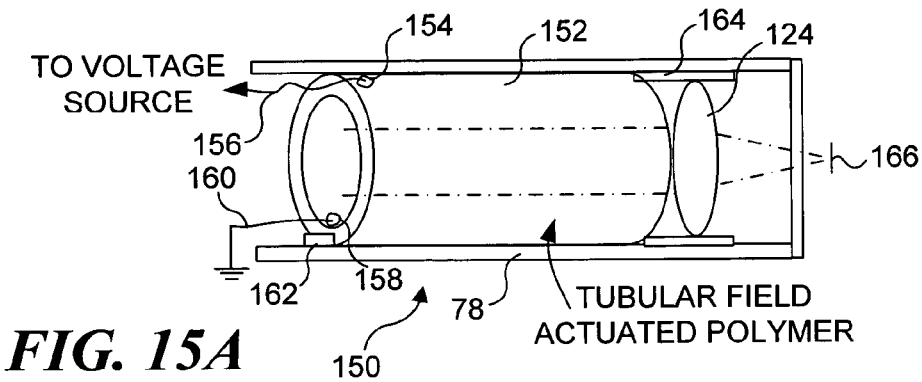
FIGS. 15A and 15B schematically illustrate a portion of an optical fiber scanner that uses a tubular field actuated polymer driver to vary the scanning depth (i.e., the depth of the focal point of the optical fiber scanner)
Figure 15B:
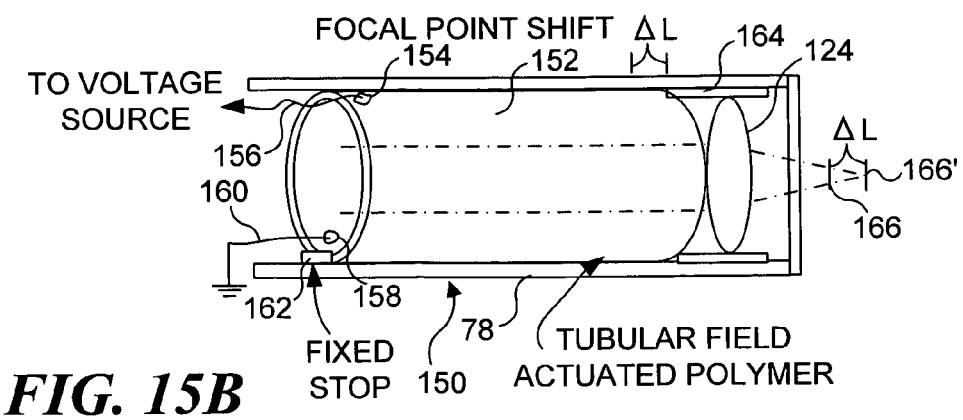

FIGS. 15A and 15B illustrate an embodiment 150 in which a tubular field actuated polymer 152 is used to move a lens longitudinally to vary the depth at which the focus point is located in a subject being scanned. The material from which tubular field actuated polymer 152 is fabricated has the characteristic that in the presence of an applied voltage, it changes both in thickness and in length. Therefore, in embodiment 150, a lead 156 is coupled to a terminal 154 on an outer surface of the tubular field actuated polymer, while a terminal 158, which is disposed on the interior surface of the tubular field actuated polymer, is coupled to ground. Also, the proximal end of tubular field actuated polymer 152 is disposed against a stop 162 preventing it from moving within metal hypodermic tubing 78. The distal end of the tubular field actuated polymer is connected to a support 164 that holds lens 124 and slides axially, thus axially moving lens 124 to vary the focus of the optical system. When an appropriate voltage is applied to terminals 154 and 158, the tubular field actuated polymer becomes thinner, but lengthens by an amount $\Delta L$. This change in length causes support 164 to slide distally within the metal hypodermic tubing, shifting the location of the focal point of lens 124 from a point 166 to a point 166', by an amount equal to $\Delta L$. The voltage level applied to terminals 154 and 158 can be selectively controllably to vary the position of the focal point of lens 124 by a desired amount. This same approach can alternatively be applied to any other lens within the optical system, to similarly vary the longitudinal position of the focal point, and thereby provide depth focus tracking.

Figure 16A:
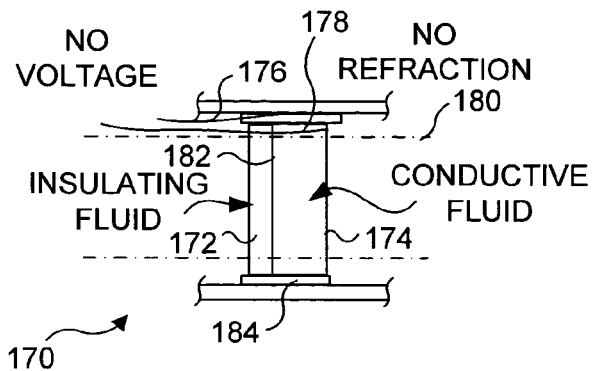
FIGS. 16A and 16B schematically illustrate a portion of an embodiment in which the refraction of a fluid lens is controlled by an applied voltage to selectively vary the longitudinal location of the focal point of the lens at different depths.
Figure 16B:
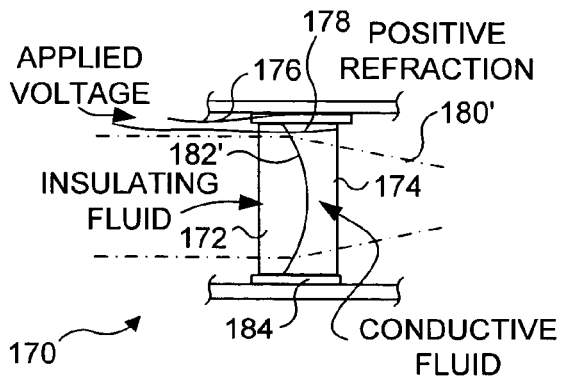

Yet another embodiment 170 is illustrated in FIGS. 16A and 16B, for adjusting the depth of the focal point in a subject. In this embodiment, a deformable lens is used, for which the focal length can be varied for performing focus tracking. In FIGS. 16A and 16B, an exemplary fluid lens having two volumes 172 and 174 that are separated by an interface 182 (FIG. 16A) is used to vary the refraction of a light beam 180 by the fluid lens. Volume 172 is filled with an insulating fluid, while volume 174 is filled with a conductive fluid. A lead 176 is coupled to a conductive sleeve 184 disposed around the fluid lens doublet. The conductive sleeve has an insulator (not shown) separating the electrode and fluid lens doublet. A lead 178 is coupled to the conductive fluid volume 174. As shown in FIG. 16A, no voltage is applied between leads 176 and 178, and the fluid lens generally does not refract light 180 passing through it. However, as shown in FIG. 16B, when an appropriate voltage is applied to leads 176 and 178 interface 182' distorts, causing a change in the shape of volumes 172 and 174 that refract light 180' passing through the fluid lens, thereby changing the longitudinal depth at which the light is focused. Thus, by controlling the voltage applied to leads 176 and 178, it is possible to provide depth focus tracking, in accord with the present invention. It should be understood that the focus size and depth of focus can be changed using this scheme for focus tracking.

Figure 16C:
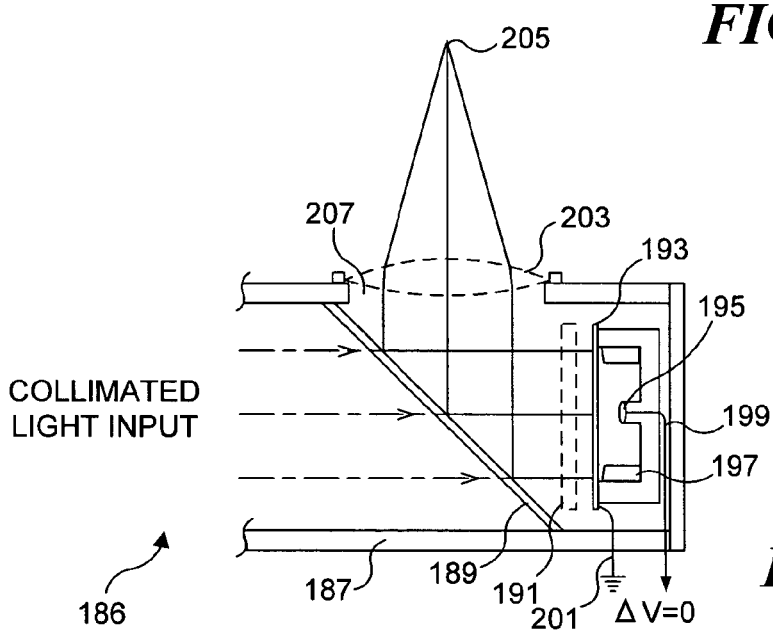
FIGS. 16C and 16D schematically illustrate a portion of an embodiment of a side scanning endoscope in which the refraction of a deformable membrane mirror (DMM) is controlled by an applied voltage to selectively vary the focal point of the DMM and thus, of the endoscope, at different depths in tissue to the side of the endoscope longitudinal axis.
Figure 16D:
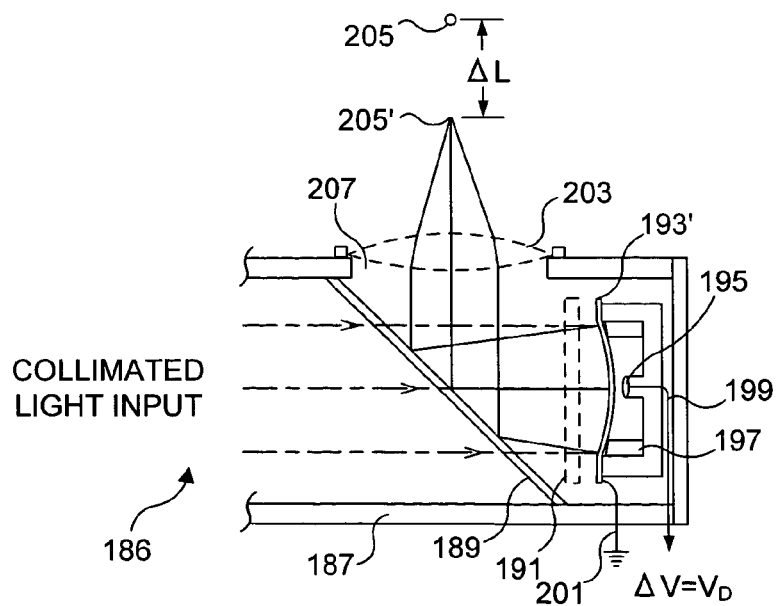

FIGS. 16C and 16D illustrate a schematic view for an embodiment 186 comprising a side viewing endoscope 187 according to the present invention, in which a deformable membrane mirror (DMM) 193 is used with a beamsplitter 189 and employed to vary a depth of the focal point of the endoscope in the tissue (not shown) of a subject that is to the side of the endoscope, thereby providing depth focus tracking in this tissue. Beamsplitter 189 changes the optical path of the light from being along the longitudinal axis of endoscope 187, by directing the light from the DMM laterally toward the side and through window 207. A lead 201 couples DMM 193 to ground, while a lead 199 connects to an electrostatic actuator 195, which is mounted behind the DMM. A differential voltage, $\Delta V$, of up to about 100 VDC can thus be selectively applied between the DMM and the electrostatic actuator to deflect the DMM from its planar state. Two stops 197 are included peripherally around the electrostatic actuator, to limit the deflection of the DMM. If the DMM is the final lens in the endoscope and input light is collimated and not converging, an optional lens 203 can be employed to focus light passing through a window 207 in the side of endoscope 187 toward the focal point in the tissue of the subject, since focusing of collimated light directed to the side is required when the DMM is in its planar state. Also, beamsplitter 189 can be of the simple 50/50 cube type that is edged to a cylindrical shape. This type of beamsplitter will have a substantial loss from twice splitting the light, i.e., the light input to the endoscope as well as the light the reflected from the DMM. Optionally, to provide a substantial increase in efficiency, the light can be linearly polarized, and a $\lambda/4$ plate 191 disposed in the light path between a polarizing cube beamsplitter (in the location shown for beamsplitter 189) and DMM 193, which will cause a $\lambda/2$ shift after the light passes through the $\lambda/4$ plate twice, but will transmit almost all of the input light to the tissue at the side. However, use of $\lambda/4$ plate 191 increases the cost and complexity of the endoscope.

In FIG. 16C, the value of ΔV is equal to zero, and DMM 193 is generally planar, resulting in a focal point 205 in the tissue to the side of the endoscope. In contrast, in FIG. 16D, a ΔV equal to $V_D$ has been applied, causing a change from the planar configuration of the DMM in FIG. 16C, to a parabolic deflection, as indicated by a DMM 193' in FIG. 16D. In FIG. 16D, the focus point is shifted to a lower depth in the tissue to the side of the endoscope, as indicated by a focal point 205', which changed the depth of focus relative to the planar state of the DMM in FIG. 16C by ΔL. Beamsplitters are available that can split non-collimated light, so optional lens 203 will not be required if such a beamsplitter is used, or if the DMM is configured so that it is at least partially concave when ΔV equals zero and becomes more concave when the value of ΔV is equal to $V_D$>zero. It should be understood that the focus size and depth of focus can be changed using this scheme for focus tracking.

Figure 17:
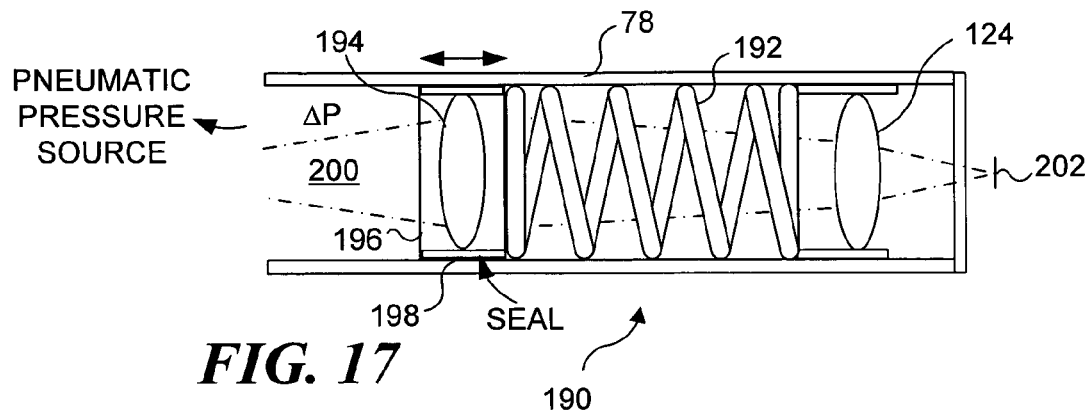
FIG. 17 is a schematic cut-away view of another embodiment, showing how a varying pneumatic pressure is applied to a lens carrier, producing a force that varies the location of the focal point of a lens, to enable transverse scanning at different depths in the present invention.

FIG. 17 illustrates an embodiment 190 in which a lens 194 is mounted within a transparent carrier 196 that slides longitudinally inside metal hypodermic tubing 78 in response to a pressure, ΔP, applied from a proximal pressure source (not shown) to a volume 200. Volume 200 is proximal the transparent carrier. A seal 198 around the periphery of transparent carrier 196 ensures that pressurized pneumatic fluid does not leak past the periphery of the transparent carrier. A helical spring 192 provides a restoring bias force that resists the distally directed force acting on the transparent carrier as a result of the pressure in volume 200. Lens 124 is fixed in position. As lens 194 is moved longitudinally in response to a change in the pressure within volume 200, the focal point also shifts longitudinally, enabling the depth focus tracking to be varied selectively as a function of the applied pressure. It should be understood that the focus size and depth of focus can be changed using this scheme for focus tracking.

Figure 18:
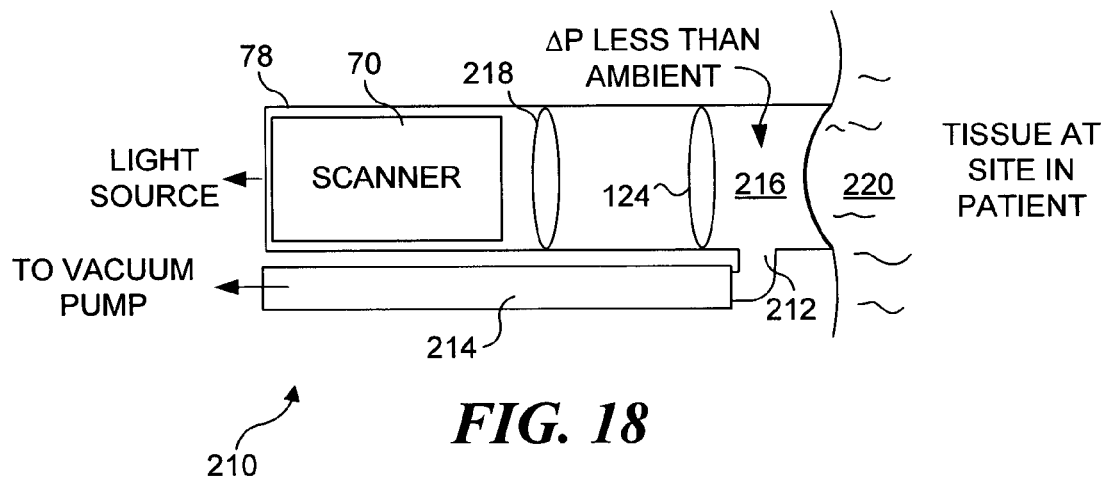
FIG. 18 is a schematic cut-away view of yet another embodiment in which a vacuum source is applied to vary the longitudinal position of tissue drawn into an open distal end of the optical fiber scanner, to vary the longitudinal location of the focal point for scanning at different depths in the tissue.

Finally, in FIG. 18, an embodiment 210 includes a lens 218 and lens 124, both of which are fixed in place. A port 212 is formed in metal hypodermic tube 78, distal of lens 124. Port 212 is coupled through a flexible tube 214 to a vacuum pump or other suitable controlled vacuum source (not shown) that can vary the level of vacuum applied to a volume 216 that is distal of lens 124. The open end of metal hypodermic tube 78 is placed in sealing contact with tissue 220, and a desired level of vacuum applied. The reduced pressure within volume 216 draws tissue 220 into the open end of the device to an extent that can vary the depth at which light from lens 124 is focused within the tissue. Thus, by controlling the level of the vacuum applied to volume 216, the depth focus tracking is readily controlled in accord with the present invention, to enable transverse scanning at successive depths in the tissue. It will be understood that the image quality might be affected by the change in negative pressure applied to the tissue.

Although the present invention has been described in connection with the preferred form of practicing it and modifications thereto, those of ordinary skill in the art will understand that many other modifications can be made to the invention within the scope of the claims that follow. Accordingly, it is not intended that the scope of the invention in any way be limited by the above description, but instead be determined entirely by reference to the claims that follow.

The invention in which an exclusive right is claimed is defined by the following:

1. A method for using an optical fiber scanner for carrying out rapid scanning during imaging of a subject to carry out either optical coherence tomography, confocal imaging, or multiphoton excitation imaging of the subject, comprising the steps of:

(a) advancing the optical fiber scanner to a position adjacent to the subject, the optical fiber scanner including an actuator cantilevered from a fixed mounting base, and an optical fiber, a portion of the optical fiber being cantilevered from the actuator to form a cantilevered optical fiber, the actuator including a plurality of pairs of drivers disposed in a predefined pattern to drive the cantilevered optical fiber in regard to a plurality of axes of the actuator;

(b) actuating the cantilevered optical fiber such that it rapidly moves generally in a two-dimensional area scanning path comprising a desired scanning pattern and such that it is driven to vibrate at one of a resonant frequency, and a near-resonant frequency of the cantilevered optical fiber, a combination of the actuator that is cantilevered and the cantilevered optical fiber resulting in a large displacement of the cantilevered optical fiber as it moves in the two-dimensional scanning path at a rapid rate, the step of actuating comprising the step of applying a signal that actuates the plurality of pairs of drivers to drive the cantilevered optical fiber in the desired scanning pattern;

(c) conveying light through the cantilevered optical fiber and emitting the light from a distal portion of the cantilevered optical fiber, to illuminate the subject as the light emitted from the distal portion of the cantilevered optical fiber scans the subject in the desired scanning pattern at a desired depth within the subject;

(d) moving a focal point of the optical fiber scanner generally along an axis that is substantially orthogonal to the plane of the desired scanning pattern, to scan at a different desired depth within the subject; and (e) repeating step (b) at the different desired depth.

2. The method of claim 1, wherein the step of actuating causes the cantilevered optical fiber to move back and forth generally laterally relative to a longitudinal axis of the optical fiber scanner.

3. The method of claim 1, wherein the step of actuating further comprises the step of driving the cantilevered optical fiber to move in two generally orthogonal directions, both of which are generally orthogonal to a longitudinal axis of the optical fiber scanner.

4. The method of claim 1, wherein the focal point of the optical fiber scanner is moved to a different depth at a substantially slower rate than the cantilevered optical fiber is actuated to move it generally in the plane, for scanning the subject in the desired pattern.

5. The method of claim 1, wherein the focal point of the optical fiber scanner is moved longitudinally in a stepwise manner, repeating steps (b) and (c) for each different depth desired, so that the cantilevered optical fiber scans, generally transversely, at a plurality of different depths.

6. The method of claim 1, further comprising the step of employing one of an electro-optic phase modulator and an acousto-optic modulator in one of a sample arm and a reference arm, when carrying out optical coherence tomography.

7. The method of claim 1, wherein while carrying out multiphoton excitation imaging with a light source that comprises a laser, further comprising the step of pre-chirping the laser pulses to pre-compensate for a pulse broadening of the light from the laser before the light reaches the focal point within the subject.

8. The method of claim 1, further comprising the step of focusing light passing through the distal portion of the cantilevered optical fiber using a lens optically linked thereto.

9. The method of claim 8, wherein the lens optically linked to the distal portion of the cantilevered optical fiber comprises at least one of a refractive type lens, a graded index (GRIN) type lens, and a miniature compound achromatic lens having a plurality of lens elements.

10. The method of claim 1, further comprising the step of focusing and collecting light passing through the distal portion of the cantilevered optical fiber using a lens that is longitudinally movable relative to the distal portion of the cantilevered optical fiber, to adjust the focal point of the optical fiber scanner.

11. The method of claim 1, wherein the step of moving the focal point of the optical fiber scanner includes at least one of the steps of:
(a) actuating an elastomeric polymer that changes length in response to an electric potential, shifting the focal point longitudinally;
(b) changing a focus of a variable focus fluid lens that shifts the focal point longitudinally, in response to an electric potential;
(c) driving a motor to rotate a shaft that shifts the focal point longitudinally;
(d) applying one of a hydraulic and pneumatic pressure to overcome a spring tension, causing the focal point to move;
(e) controlling a pressure applied to vary a separation between tissue at the subject and the distal portion of the cantilevered optical fiber, shifting the focal point longitudinally; and
(f) changing a focus of a deformable membrane mirror that shifts the focal point to vary the depth in the subject, in response to an electric potential.

12. The method of claim 1, further comprising the step of substantially reducing back reflections by carrying out at least one of the steps of creating an angled bevel on a distal end of the cantilevered optical fiber through which light is conveyed in the optical fiber scanner, and applying an anti-reflection coating to one or more possibly reflective surfaces.

13. The method of claim 1, wherein the step of advancing the optical fiber scanner comprises the step of delivering the optical fiber scanner to a site with or without an endoscope.

14. A compact optical fiber scanner adapted for use in carrying out a rapid transverse scan while imaging a subject during either optical coherence tomography, confocal imaging, or multiphoton excitation imaging of the subject, comprising:
(a) a light source that produces light;
(b) an optical fiber having a proximal end and a distal end, the light source being optically coupled to the proximal end of said optical fiber, said distal end of the optical fiber being adapted to be positioned adjacent to a subject;
(c) a scanning actuator disposed adjacent to the distal end of a longitudinal axis of the optical fiber, a portion of the optical fiber being cantilevered from the scanning actuator, said scanning actuator driving the cantilevered portion of the optical fiber that is disposed at the distal end of the optical fiber to vibrate in two generally orthogonal directions, both of which are generally orthogonal to a longitudinal axis of the optical fiber, causing light produced by the light source that is conveyed through the optical fiber and is emitted from a distal end of the cantilevered portion, to scan a region of interest in a desired scanning pattern, wherein said scanning actuator drives the cantilevered portion of the optical fiber to vibrate at one of a resonant frequency, and a near-resonant frequency, the scanning actuator comprising a tubular piezoelectric driver that is configured to be axially symmetric about the portion of the optical fiber that is cantilevered from the scanning actuator, and concentric about the longitudinal axis of the optical fiber, to thereby achieve a compact configuration;
(d) a focusing lens disposed proximate to and distal of the distal end of the cantilevered portion of the optical fiber, said focusing lens being longitudinally spaced apart from the scanning actuator;
(e) a focal point displacer that moves a focal point of the focusing lens to change a disposition of a focal point of the optical fiber scanner, to scan at a different depth in a subject after the scanning actuator and cantilevered portion of the optical fiber have completed scanning at a previous depth; and
(f) a light detector that responds to light that was reflected from a subject and collected by the optical fiber scanner, producing a signal.

15. The optical fiber scanner of claim 14, wherein the scanning actuator drives the cantilevered portion of the optical fiber to vibrate back and forth generally laterally relative to a longitudinal axis of the optical fiber scanner.

16. The optical fiber scanner of claim 14, wherein the scanning actuator drives the cantilevered portion of the optical fiber to vibrate in a two-dimensional, area scanning path comprising the desired scanning pattern.

17. The optical fiber scanner of claim 14, further comprising a reference arm coupled to a splitter in an optical path of the light produced by the source, so that light from the source is split between a measuring arm that includes the distal end of the optical fiber and the reference arm, the reference arm including one of an electro-optic phase modulator and an acousto-optic frequency modulator for use in carrying out optical coherence tomography.

18. The optical fiber scanner of claim 14, wherein the focal point displacer changes the focal point of the focusing lens at a substantially slower rate than the distal end of the cantilevered portion of the optical fiber is caused to vibrate in the desired pattern by the scanning actuator.

19. The optical fiber scanner of claim 14, wherein the focal point displacer changes the disposition of the focal point of the focusing lens in one of a stepwise and a continuous manner, to focus at each different depth desired.

20. The optical fiber scanner of claim 14, wherein the focal point displacer changes a separation between the distal end of the cantilevered portion of the optical fiber and the focusing lens to change the disposition of the focal point in order to scan at each different depth desired.

21. The optical fiber scanner of claim 14, wherein the focal point displacer comprises at least one of:
(a) an elastomeric polymer coupling a lens to the optical fiber scanner, the elastomeric polymer changing length in response to an electric potential applied to the elastomeric polymer, causing the disposition of the focal point to shift longitudinally;
(b) a variable focus lens that shifts the disposition of the focal point of the optical fiber scanner in response to an electric potential applied to the variable focus lens, causing the disposition of the focal point to shift longitudinally;
(c) a motor that is drivingly coupled to a shaft for shifting the disposition of the focal point of the optical fiber scanner as the shaft is rotated by the motor, causing the disposition of the focal point to shift longitudinally;
(d) a source of one of a hydraulic and pneumatic pressure applied to a volume to overcome a spring bias, causing the disposition of the focal point to shift longitudinally;
(e) a vacuum source coupled to an enclosed space disposed between tissue at a subject being scanned and a distal end of the cantilevered portion of the optical fiber, variation in a level of vacuum applied to the enclosed space causing the disposition of the focal point to shift longitudinally; and (f) a beamsplitter that directs a portion of the light from the light source transversely relative to a longitudinal axis of the optical fiber scanner, and a deformable membrane mirror that shifts the disposition of the focal point of the optical fiber scanner in response to an electric potential applied to the deformable membrane mirror, causing the disposition of the focal point to change in the direction in which the portion of the light is penetrating into the subject.

22. The optical fiber scanner of claim 14, wherein the distal end of the cantilevered portion of the optical fiber includes at least one of an angled bevel and an anti-reflection coating for the wavelengths of interest.

23. The optical fiber scanner of claim 14, wherein the scanning actuator comprises a piezoelectric actuator.

24. The optical fiber scanner of claim 14, further comprising one of an analog and a digital demodulator for demodulating the signal produced by the light detector, for use in optical coherence tomography.

25. The optical fiber scanner of claim 14, further comprising a tubular housing disposed about a distal end of the cantilevered portion of the optical fiber.

26. The optical fiber scanner of claim 14, further comprising a lens optically linked to the distal end of the cantilevered portion of the optical fiber.

27. The optical fiber scanner of claim 26, wherein the lens optically linked to the distal end of the cantilevered portion of the optical fiber comprises one of a refractive type lens, a graded index (GRIN) type lens, and a miniature compound achromatic lens.

28. An optical fiber scanner adapted for use in carrying out a rapid transverse scan while imaging a subject during either optical coherence tomography, confocal imaging, or multiphoton excitation imaging of the subject, comprising:
(a) a light source that produces light;
(b) an optical fiber having a proximal end and a distal end, the light source being optically coupled to the proximal end of said optical fiber, said distal end of the optical fiber being adapted to be positioned adjacent to a subject;
(c) a piezoelectric actuator having a proximal end and a distal end, the proximal end of the piezoelectric actuator being supported by a fixed mounting base and being cantilevered therefrom, the distal end of the optical fiber including a cantilevered portion that extends distally from the distal end of the piezoelectric actuator, said piezoelectric actuator including a plurality of pairs of drivers disposed in a predefined pattern in regard to a plurality of axes of the actuator, thereby configuring the actuator to drive the cantilevered portion of the optical fiber that is disposed at the distal end of the optical fiber to vibrate in two generally orthogonal directions, both of which are generally orthogonal to a longitudinal axis of the optical fiber, causing light produced by the light source that is conveyed through the optical fiber and is emitted from a distal end of the cantilevered portion, to scan a region of interest in a desired scanning pattern;
(d) a focusing lens disposed proximate to the distal end of the cantilevered portion of the optical fiber;
(e) a focal point displacer that causes a relative movement between the distal end of that cantilevered portion of the optical fiber and the focusing lens, to change a disposition of a focal point of the optical fiber scanner, enabling the optical fiber scanner to scan at a different depth in a subject after the scanning actuator and cantilevered portion of the optical fiber have completed scanning at a previous depth; and
(f) a light detector that responds to light reflected from a subject and collected by the optical fiber, producing a signal useful for imaging the subject.

29. A method for using an optical fiber scanner for carrying out rapid scanning during imaging of a subject to carry out one of optical coherence tomography, confocal imaging, and multiphoton excitation imaging of the subject, comprising the steps of:
(a) advancing the optical fiber scanner to a position adjacent to the subject, the optical fiber scanner including an optical fiber having a proximal end and a distal end, said optical fiber scanner further having an actuator disposed symmetrically about a longitudinal axis of the optical fiber and disposed adjacent to the distal end such that the distal end of the optical fiber is cantilevered from the actuator to form a cantilevered optical fiber that is configured to be actuated to vibrate so that the cantilevered optical fiber moves in a desired scanning pattern to scan the subject, the cantilevered optical fiber emitting light from a distal end of the cantilevered optical fiber that is focused using a lens that is disposed at or distally beyond the distal end of the optical fiber and longitudinally spaced apart from the actuator, to illuminate the subject as the light emitted from the distal portion of the cantilevered optical fiber scans the subject in the desired scanning pattern at a depth determined by a focal point of the optical fiber scanner;
(b) actuating the cantilevered optical fiber symmetrically about the longitudinal axis using a tubular actuator that is concentrically disposed about the cantilevered optical fiber, thereby achieving a compact configuration that causes the cantilevered optical fiber to vibrate such that the cantilevered optical fiber rapidly moves generally in a two-dimensional area scanning path comprising the desired scanning pattern, at a frequency greater than 1.0 kilohertz;
(c) moving the focal point of the optical fiber scanner generally along an axis that is substantially orthogonal to a plane of the desired scanning pattern, to scan at a different depth within the subject, the focal point moving at a substantially slower rate than that at which the cantilevered optical fiber scans in the desired scanning pattern; and
(d) repeating step (b) to scan at the different depth.

30. A method for using an optical fiber scanner for carrying out rapid scanning, to carry out any of optical coherence tomography imaging, confocal imaging, or multiphoton excitation imaging of a subject, comprising the steps of:
(a) advancing the optical fiber scanner to a position adjacent to the subject, the optical fiber scanner including an actuator cantilevered from a fixed mounting base, and an optical fiber, a portion of the optical fiber being cantilevered from the actuator to form a cantilevered optical fiber, the actuator including a plurality of pairs of drivers disposed in a predefined pattern to drive the cantilevered optical fiber in regard to a plurality of axes of the actuator, thereby enabling the actuator to drive the cantilevered optical fiber to vibrate so that the cantilevered optical fiber moves in a desired scanning pattern to scan the subject at a depth determined by a focal point of the optical fiber scanner, the cantilevered optical fiber conveying light that is emitted from a distal portion of the cantilevered optical fiber, to illuminate the subject as the light emitted from the distal portion of the cantilevered optical fiber scans the subject in the desired scanning pattern, wherein the desired scanning pattern is either a spiral scan or a helical scan;

(b) actuating the cantilevered optical fiber such that it rapidly moves generally in a two-dimensional area scanning path comprising the desired scanning pattern and such that it is driven to vibrate at either a resonant frequency, or a near-resonant frequency of the cantilevered optical fiber, a combination of the actuator that is cantilevered and the cantilevered optical fiber resulting in a large displacement of the cantilevered optical fiber as it moves in the two-dimensional scanning path at a rapid rate;

(c) moving the focal point of the optical fiber scanner generally along an axis that is substantially orthogonal to the plane of the desired scanning pattern, to scan at a different depth within the subject; and (d) repeating step (b) at the different depth.

* * * * *

UNITED STATES PATENT AND TRADEMARK OFFICE
CERTIFICATE OF CORRECTION

PATENT NO. : 7,616,986 B2 Page 1 of 1
APPLICATION NO. : 10/880008
DATED : November 10, 2009
INVENTOR(S) : Seibel et al.

It is certified that error appears in the above-identified patent and that said Letters Patent is hereby corrected as shown below:

| | |
|---|---|
| Column 1, line 18 | The paragraph under the heading "Government Rights" should be deleted and replaced in its entirety with the following: --This invention was made with government support under Federal Reporting note 1 R21 CA96633-01 and Federal Reporting note 1 R21 CA094303-01A1 awarded by the National Institutes of Health. The Government has certain rights in the invention.-- |
| Column 3, line 42 | after "objective" (2nd occurrence) insert --lens-- |
| Column 8, line 61 | "have" should read --having-- |

Signed and Sealed this

Twenty-seventh Day of April, 2010

David J. Kappos
*Director of the United States Patent and Trademark Office*